(12) United States Patent
Gu et al.

(10) Patent No.: US 11,853,013 B2
(45) Date of Patent: Dec. 26, 2023

(54) SYSTEMS AND METHODS FOR INDICATING THE TIME ELAPSED SINCE THE OCCURRENCE OF A TRIGGERING EVENT

(71) Applicant: Johnson & Johnson Vision Care, Inc., Jacksonville, FL (US)

(72) Inventors: Frank Gu, Toronto (CA); Paul Chen, Toronto (CA)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 756 days.

(21) Appl. No.: 16/901,113

(22) Filed: Jun. 15, 2020

(65) Prior Publication Data

US 2021/0389731 A1    Dec. 16, 2021

(51) Int. Cl.
| | |
|---|---|
| *G04F 13/02* | (2006.01) |
| *G01N 31/22* | (2006.01) |
| *G01N 21/78* | (2006.01) |
| *B82Y 20/00* | (2011.01) |
| *A61K 33/38* | (2006.01) |
| *A61L 15/56* | (2006.01) |
| *A61L 15/44* | (2006.01) |
| *G01N 21/77* | (2006.01) |

(52) U.S. Cl.
CPC ........... *G04F 13/02* (2013.01); *G01N 31/229* (2013.01); *A61K 33/38* (2013.01); *A61L 15/44* (2013.01); *A61L 15/56* (2013.01); *B82Y 20/00* (2013.01); *G01N 21/77* (2013.01); *G01N 21/78* (2013.01)

(58) Field of Classification Search
CPC ...... G04F 13/02; G01N 31/229; G01N 21/78; G01N 21/77; B82Y 20/00; G02C 7/021; G02C 7/04; A61L 15/44; A61L 15/56; A61K 33/38
See application file for complete search history.

(56) References Cited

U.S. PATENT DOCUMENTS

| | | | |
|---|---|---|---|
| 3,408,429 | A | 10/1968 | Wichterle |
| 3,660,545 | A | 5/1972 | Wichterle |
| 3,808,178 | A | 4/1974 | Gaylord |
| 4,028,876 | A | 6/1977 | Delatorre |

(Continued)

FOREIGN PATENT DOCUMENTS

| | | |
|---|---|---|
| EP | 0080539 B1 | 6/1983 |
| EP | 2626195 A1 | 8/2013 |

(Continued)

OTHER PUBLICATIONS

Bruchez et al, "Semiconductor Nanocrystals as Fluorescent Biological Lables," Science, vol. 281, pp. 2013-2016, Sep. 25, 1998.

(Continued)

*Primary Examiner* — John Fitzgerald
*Assistant Examiner* — Tania Courson
(74) *Attorney, Agent, or Firm* — Raef M. Shaltout

(57) ABSTRACT

Described are systems and methods which can be used to indicate the period of time elapsed since the occurrence of a triggering event. More particularly, this application relates to systems and methods which can be used to visually indicate the time period elapsed since an article has been removed from its packaging. The system can include an indicator disposed on or within the article and a trigger disposed within the receptacle and in contact with the indicator. The article may be enclosed within a sealable receptacle of the package. The indicator is responsive to a change in a concentration of the trigger in contact with the indicator.

46 Claims, 16 Drawing Sheets

(56) References Cited

U.S. PATENT DOCUMENTS

| | | |
|---|---|---|
| 4,113,224 A | 9/1978 | Clark et al. |
| 4,120,570 A | 10/1978 | Gaylord |
| 4,136,250 A | 1/1979 | Mueller et al. |
| 4,153,641 A | 5/1979 | Deichert et al. |
| 4,197,266 A | 4/1980 | Clark et al. |
| 4,436,887 A | 3/1984 | Chromecek et al. |
| 4,495,313 A | 1/1985 | Larsen |
| 4,659,782 A | 4/1987 | Spinelli |
| 4,659,783 A | 4/1987 | Spinelli |
| 4,740,533 A | 4/1988 | Su et al. |
| 4,889,664 A | 12/1989 | Kindt-Larsen et al. |
| 4,910,277 A | 3/1990 | Bambury et al. |
| 5,006,622 A | 4/1991 | Kunzler et al. |
| 5,034,461 A | 7/1991 | Lai et al. |
| 5,039,459 A | 8/1991 | Kindt-Larsen et al. |
| 5,070,215 A | 12/1991 | Bambury et al. |
| 5,236,969 A | 8/1993 | Kunzler et al. |
| 5,244,981 A | 9/1993 | Seidner et al. |
| 5,270,418 A | 12/1993 | Kunzler et al. |
| 5,298,533 A | 3/1994 | Nandu et al. |
| 5,314,960 A | 5/1994 | Spinelli et al. |
| 5,331,067 A | 7/1994 | Seidner et al. |
| 5,371,147 A | 12/1994 | Spinelli et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,824,719 A | 10/1998 | Kunzler et al. |
| 5,849,811 A | 12/1998 | Nicolson et al. |
| 5,962,548 A | 10/1999 | Vanderlaan et al. |
| 5,965,631 A | 10/1999 | Nicolson et al. |
| 5,990,479 A | 11/1999 | Weiss et al. |
| 5,998,498 A | 12/1999 | Vanderlaan et al. |
| 6,020,445 A | 2/2000 | Vanderlaan et al. |
| 6,051,207 A | 4/2000 | Klaveness et al. |
| 6,087,415 A | 7/2000 | Vanderlaan et al. |
| 6,367,929 B1 | 4/2002 | Maiden et al. |
| 6,420,453 B1 | 7/2002 | Bowers et al. |
| 6,423,761 B1 | 7/2002 | Bowers et al. |
| 6,767,979 B1 | 7/2004 | Muir et al. |
| 6,822,016 B2 | 11/2004 | McCabe et al. |
| 6,851,808 B2* | 2/2005 | Heacock ............... A61B 3/125 351/219 |
| 6,867,245 B2 | 3/2005 | Iwata et al. |
| 6,943,203 B2 | 9/2005 | Vanderlaan et al. |
| 6,951,894 B1 | 10/2005 | Nicolson et al. |
| 7,052,131 B2 | 5/2006 | McCabe et al. |
| 7,247,692 B2 | 7/2007 | Laredo |
| 7,249,848 B2 | 7/2007 | Laredo et al. |
| 7,396,890 B2 | 7/2008 | Zanini et al. |
| 7,461,937 B2 | 12/2008 | STeffen et al. |
| 7,468,398 B2 | 12/2008 | Nicolson et al. |
| 7,538,146 B2 | 5/2009 | Nicolson et al. |
| 7,553,880 B2 | 6/2009 | Nicolson et al. |
| 7,572,841 B2 | 8/2009 | Chen et al. |
| 7,666,921 B2 | 2/2010 | McCabe et al. |
| 7,691,916 B2 | 4/2010 | McCabe et al. |
| 7,786,185 B2 | 8/2010 | Rathore et al. |
| 7,825,170 B2 | 11/2010 | Steffen et al. |
| 7,915,323 B2 | 3/2011 | Awasthi et al. |
| 7,934,830 B2 | 5/2011 | Blackwell et al. |
| 7,956,131 B2 | 6/2011 | Arnold et al. |
| 7,994,356 B2 | 8/2011 | Awasthi et al. |
| 8,022,158 B2 | 9/2011 | Rathore et al. |
| 8,033,715 B2* | 10/2011 | Perez-Luna ............... G01K 3/04 374/102 |
| 8,138,290 B2 | 3/2012 | Blackwell et al. |
| 8,163,206 B2 | 4/2012 | Chang et al. |
| 8,273,802 B2 | 9/2012 | Laredo et al. |
| 8,385,998 B2 | 2/2013 | Zhang et al. |
| 8,389,597 B2 | 3/2013 | Blackwell et al. |
| 8,399,538 B2 | 3/2013 | Steffen et al. |
| 8,415,404 B2 | 4/2013 | Nicolson et al. |
| 8,420,711 B2 | 4/2013 | Awasthi et al. |
| 8,450,387 B2 | 5/2013 | McCabe et al. |
| 8,470,906 B2 | 6/2013 | Rathore et al. |
| 8,487,058 B2 | 7/2013 | Liu et al. |
| 8,507,577 B2 | 8/2013 | Zanini et al. |
| 8,568,626 B2 | 10/2013 | Nicolson et al. |
| 8,637,621 B2 | 1/2014 | Iwata et al. |
| 8,702,237 B2* | 4/2014 | Heacock ............... G02C 7/04 351/159.28 |
| 8,703,891 B2 | 4/2014 | Broad |
| 8,770,746 B2* | 7/2014 | Pasternak ............... G02C 7/049 351/159.28 |
| 8,911,080 B2* | 12/2014 | Spaulding ............... G02C 7/021 351/159.28 |
| 8,937,110 B2 | 1/2015 | Alli et al. |
| 8,937,111 B2 | 1/2015 | Alli et al. |
| 8,940,812 B2 | 1/2015 | Reboul et al. |
| 8,980,972 B2 | 3/2015 | Driver |
| 9,005,890 B1 | 4/2015 | Bhethanabotla et al. |
| 9,056,878 B2 | 6/2015 | Fujisawa et al. |
| 9,057,821 B2 | 6/2015 | Broad et al. |
| 9,125,808 B2 | 9/2015 | Alli et al. |
| 9,140,825 B2 | 9/2015 | Alli et al. |
| 9,156,934 B2 | 10/2015 | Alli et al. |
| 9,170,349 B2 | 10/2015 | Mahadevan et al. |
| 9,217,813 B2 | 12/2015 | Liu et al. |
| 9,244,196 B2 | 1/2016 | Scales et al. |
| 9,244,197 B2 | 1/2016 | Alli et al. |
| 9,260,544 B2 | 2/2016 | Rathore et al. |
| 9,297,928 B2 | 3/2016 | Molock et al. |
| 9,297,929 B2 | 3/2016 | Scales et al. |
| 9,534,964 B2* | 1/2017 | Newport ............... G01K 3/04 |
| 9,739,757 B2* | 8/2017 | Taylor ............... B32B 37/185 |
| 10,324,042 B2* | 6/2019 | Heacock ............... G01N 21/78 |
| 11,467,422 B2* | 10/2022 | Heacock ............... G01N 33/52 |
| 2008/0129960 A1* | 6/2008 | Heacock ............... G02C 7/049 351/159.31 |
| 2010/0020846 A1* | 1/2010 | Kagan ............... G01N 31/229 374/161 |
| 2010/0048847 A1 | 2/2010 | Broad |
| 2011/0241229 A1 | 10/2011 | Naasani et al. |
| 2012/0244317 A1* | 9/2012 | Edwards ............... B82Y 30/00 977/773 |
| 2013/0083286 A1* | 4/2013 | Li ............... B29D 11/00317 351/159.02 |
| 2014/0135570 A1 | 5/2014 | Blair et al. |
| 2015/0000588 A1* | 1/2015 | Newport ............... G01K 3/04 116/207 |
| 2015/0002809 A1 | 1/2015 | Cohen-Tannoudji et al. |
| 2015/0036234 A1 | 2/2015 | Ben-Yakar et al. |
| 2015/0087076 A1* | 3/2015 | Heacock ............... G01N 21/78 436/164 |
| 2015/0346513 A1* | 12/2015 | Heacock ............... G02C 7/04 351/159.3 |
| 2018/0037690 A1 | 2/2018 | Aitken et al. |
| 2021/0003754 A1 | 1/2021 | Gu et al. |
| 2021/0181531 A1* | 6/2021 | Reedy ............... G02C 7/083 |
| 2022/0137038 A1* | 5/2022 | Chou ............... G06V 10/774 348/135 |

FOREIGN PATENT DOCUMENTS

| | | | |
|---|---|---|---|
| EP | 2703877 A1 | 3/2014 | |
| EP | 2787876 A1 | 10/2014 | |
| WO | 1999026299 A1 | 5/1999 | |
| WO | 0203855 A1 | 1/2002 | |
| WO | 2003022321 A2 | 3/2003 | |
| WO | 2008061992 A2 | 5/2008 | |
| WO | 2008067143 A2 | 6/2008 | |
| WO | 2011010267 A1 | 1/2011 | |
| WO | WO-2011010267 A1 * | 1/2011 | ....... B29D 11/00038 |
| WO | 2014189889 A1 | 11/2014 | |
| WO | 2014189892 A1 | 11/2014 | |

OTHER PUBLICATIONS

Compendium of Polymer Terminology and Nomenclature: IUPAC Recommendations 2008, edited by: Richard G. Jones, Jaroslav Kahovec, Robert Stepto, Edward S. Wilks, Michael Hess, Tatsuki Kitayama, and W. Val Metanomski.

(56) References Cited

OTHER PUBLICATIONS

Crivello, et al, Photoinitiators for Free Radical Cationic & Anionic Photopolymerisation, 2nd Edition, vol. III, pp. 275-298, John Wiley and Sons, New York, 1998.
PCT International Search Report, dated Aug. 14, 2020, for PCT Int'l Appln. No. PCT/IB2020/055279.
PCT International Preliminary Report on Patentability, dated Dec. 28, 2021, for PCT Int'l Appln. No. PCT/IB2020/055279.
PCT International Search Report, dated Sep. 2, 2021, for PCT Int'l Appln. No. PCT/IB2021/053557.

* cited by examiner

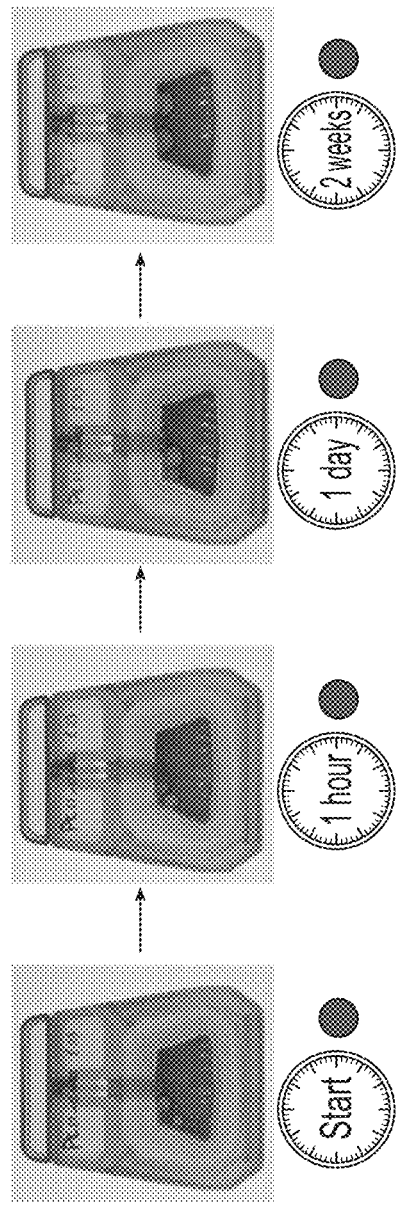

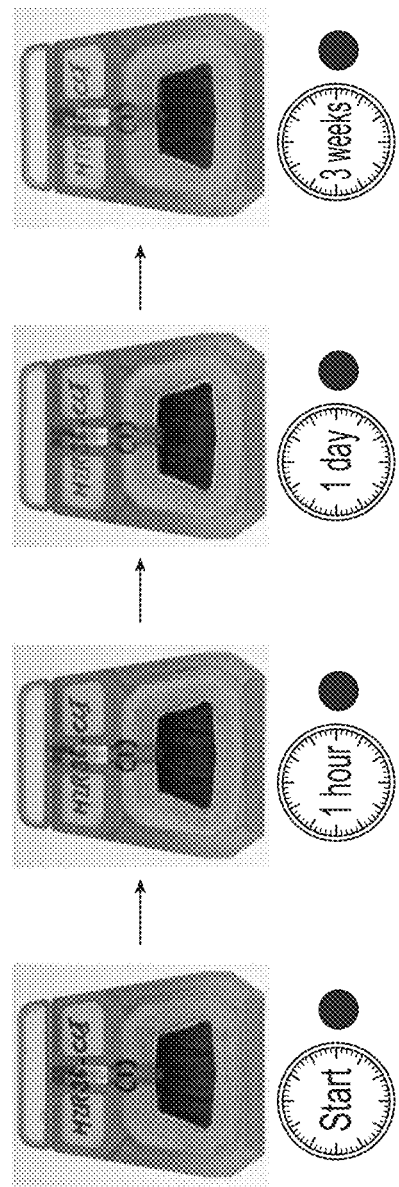

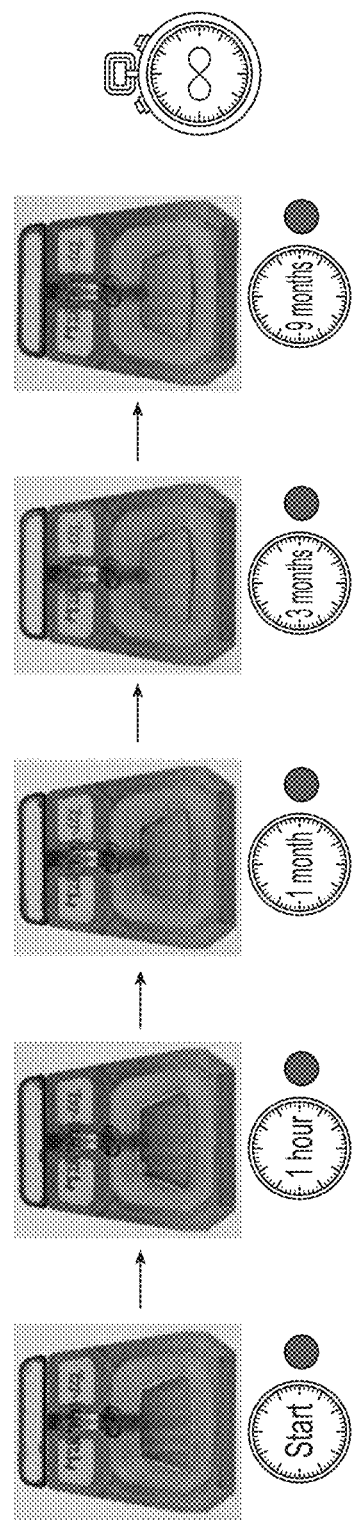

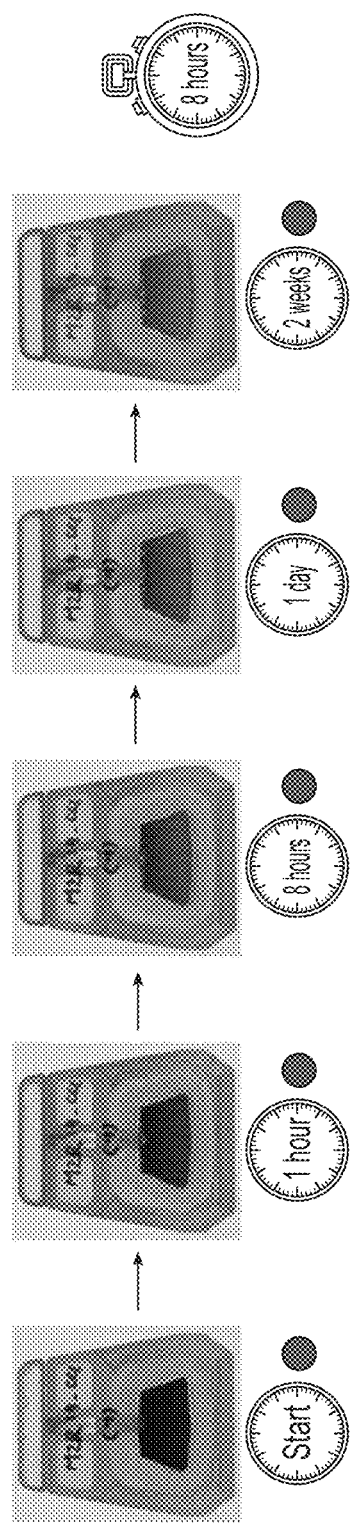

Before autoclave    After autoclave

Before autoclave   After autoclave

SYSTEMS AND METHODS FOR INDICATING THE TIME ELAPSED SINCE THE OCCURRENCE OF A TRIGGERING EVENT

BACKGROUND

Contact lenses are widely used to correct a wide variety of vision disorders, including myopia, hyperopia, and astigmatism. Contact lenses can also be used to enhance the natural appearance of the wearer's eyes. Early contact lenses were constructed or made of hard materials and were relatively expensive and fragile. In addition, the materials used to manufacture such hard contact lenses have relatively low oxygen permeability, limiting the flow of oxygen to the conjunctiva and cornea. More recently, soft contact lenses based on hydrogel materials have been developed. Soft contact lenses based on silicone hydrogels exhibit higher oxygen permeability and are generally more comfortable to wear than hard contact lenses.

Contact lenses formed form different materials can have different wear schedules and replacement schedules. "Daily wear" (DW) contact lenses are designed to be worn for one day and removed before sleeping. "Extended wear" (EW) contact lenses are designed for continuous overnight wear, typically for up to six consecutive nights. Newer materials, such as silicone hydrogels, can allow for even longer wear periods of up to 30 consecutive nights. Such longer-wear lenses are sometimes referred to as "continuous wear" contact lenses (CW). Single use lenses (sometimes called one-day or daily disposable lenses) are designed to be discarded after one use. Other disposable contact lenses are designed for replacement every two or four weeks. Other lenses are designed to be replaced quarterly, semi-annually, annually, or even less regularly.

Contact lens manufacturers and ophthalmologists recommend specific replacement times for different types of contact lenses for a variety of reasons. For example, regardless of how well the contact lenses are cleaned and maintained, contact lenses may accumulate protein, calcium and/or lipid deposits over time. These deposits may make the contact lens less comfortable to wear and may make the eye more susceptible to infection and irritation. To minimize adverse side-effects, wearers need to track the lens wear time to ensure timely replacement of contact lenses. However, at present, commercially available lenses do not include a simple indicator to provide a clear signal to a wearer that a contact lens has been used beyond its recommended wearing schedule.

Accordingly, there is a need for simple systems which can be incorporated into contact lenses to signal a wearer that a lens needs to be replaced in order to prevent wearers from exceeding the specified replacement period.

SUMMARY

Provided herein are systems and methods which can be used to indicate the period of time elapsed since the occurrence of a triggering event. More particularly, this application relates to systems and methods which can be used to visually indicate, for example, the time period elapsed since an article has been removed from its packaging, the period of time elapsed since an article or composition has been prepared, and/or the period of time that an article has been in use.

The system can include an indicator disposed on or within the article. The article may be enclosed within a sealable receptacle of a package. The system can further include a trigger disposed within the receptacle and in contact with the indicator. The indicator can be responsive to a change in a concentration of the trigger in contact with the indicator. The trigger can be present in the sealable receptacle at a static concentration.

The removal of the article from the receptacle can induce a change in concentration of the trigger in contact with the indicator. A change in the concentration of the trigger can induce an observable change in the indicator. For example, in some embodiments, the indicator can be an optical indicator (e.g., a visible indicator) in which the observable change comprises a change in the color of the indicator. In such cases, the observable change can be a change in color from a first color in the visible spectrum to a second color in the visible spectrum; a change in color from a first color outside of the visible spectrum to a second color in the visible spectrum; or a change in color from a first color in the visible spectrum to a second color outside of the visible spectrum. The observable change (e.g., the color change) can indicate that a predetermined period of time has elapsed since the article has been removed from the receptacle. In some embodiments, the predetermined period of time can be from 30 minutes to 30 days, such as from 1 hour to 30 days. Importantly, the observable change can be discrete, such that substantially all of the observable change (e.g., the color change) occurs at the predetermined period of time. For example, substantially no observable change can occur prior to the predetermined period of time. Then, the observable change can occur within a relatively short period of time at and following the predetermined period of time. For example, substantially all of the observable change can occur within 48 hours (e.g., within 24 hours, within 12 hours, within 6 hours, within 5 hours, within 4 hours, within 3 hours, within 2 hours, within 1 hour, or within 30 minutes) of the predetermined period of time.

In some embodiments, a change in the concentration of the trigger can induce two or more observable changes in this indicator, so as to indicate two or more predetermined periods of time have elapsed since the article has been removed from the receptacle. In some embodiments, the first predetermined period of time can be from 10 minutes to two weeks and wherein the second predetermined period of time is from 30 minutes to 30 days, such as from 1 hour to 30 days.

In some embodiments, the indicator can comprise a population of nanoparticles stabilized by a capping agent, and the trigger can comprise a solution including the capping agent in contact with the indicator. The population of nanoparticles can comprise a population of plasmonic nanoparticles. In some embodiments, the nanoparticles can have an average particle size of from 5 nm to 100 nm as measured by transmission electron microscopy (TEM). In some cases, the population of nanoparticles can have a homogenous particle shape. In some embodiments, the population of nanoparticles can comprise a mixture of different particle shapes. The capping agent can be non-covalently associated with the nanoparticles. In certain embodiments, the capping agent can comprise, for example, a polymer, a surfactant, or a combination thereof.

In these embodiments, when the article is removed from the receptacle and placed in contact with a solution containing a lower concentration of the trigger, the capping agent can disassociate from the nanoparticle. Dissociation of the capping agent can destabilize the colloidally dispersed nanoparticles, inducing aggregation of the nanoparticles. This can result in a change in the color of the nanoparticles. The capping agent can disassociate from the nanoparticles at a rate selected such that the color change indicates a predetermined period of time has elapsed since the article has been removed from the receptacle.

In some embodiments, the indicator can comprise a first population of nanoparticles stabilized by a first capping agent and a second population of nanoparticles stabilized by a second capping agent, and the trigger can include a solution including the first capping agent and the second capping in contact with the indicator. In these embodiments, when the article is removed from the receptacle and placed in contact with a solution containing a lower concentration of the trigger, the first capping agent can disassociate from first population of nanoparticles at a faster rate than the second capping agent can disassociate from the second population of nanoparticles. The first capping agent can disassociate from the first population nanoparticles at a first rate. The dissociation of the first capping agent can destabilize the colloidally dispersed first population of nanoparticles, inducing aggregation of the first population of nanoparticles. This aggregation can generate a first color change. The second capping agent can disassociate from the second population nanoparticles at a second rate slower than the first rate. The dissociation of the second capping agent can destabilize the colloidally dispersed second population of nanoparticles, inducing aggregation of the second population of nanoparticles. This aggregation can generate a second color change. The first rate and the second rate can be selected in combination, such that the first and second color changes indicate that two successive predetermined periods of time have elapsed since the article has been removed from the receptacle. For example, the first capping agent can disassociate from the first population of nanoparticles at a first rate selected such that the first color change indicates a first predetermined period of time has elapsed since the article has been removed from the receptacle, and the second capping agent can disassociate from the second population nanoparticles at a second rate selected such that the second color change indicates a second predetermined period of time has elapsed since the article has been removed from the receptacle.

In other embodiments, the indicator can comprise a chromophore or fluorophore in combination with a dispersant, and the trigger can comprise a solution comprising the dispersant in contact with the indicator. In some embodiments, when the article is removed from the receptacle and placed in contact with a solution containing a lower concentration of the trigger, the dispersant disassociates from the chromophore or fluorophore, thereby inducing aggregation of the chromophore and generating a color change (e.g., a red shift) or inducing aggregation of the fluorophore and generating a change (e.g., a red shift) in maximum emission wavelength.

The dispersant can disassociate from the chromophore or fluorophore at a rate selected such that the color change or change in maximum emission wavelength indicates a predetermined period of time has elapsed since the article has been removed from the receptacle. In some embodiments, the change in the concentration of the trigger induces a change in the fluorescence in the indicator. The change in fluorescence can comprise a change in maximum emission wavelength, a change in fluorescence quantum yield, a change in a shape of an emission spectra, a change in fluorescence lifetime, or a combination thereof.

In other embodiments, the indicator can comprise a fluorophore, and the trigger can comprise a solution including the quencher in contact with the indicator. In some embodiments, when the article is removed from the receptacle and placed in contact with a solution containing a lower concentration of the trigger, the quencher can disassociate from the fluorophore, thereby inducing an increase in fluorescence. The quencher can disassociate from the fluorophore at a rate selected such that the increase in fluorescence indicates a predetermined period of time has elapsed since the article has been removed from the receptacle.

In other embodiments, the indicator can comprise a first fluorophore, and the trigger can comprise a solution including a second fluorophore in contact with the indicator. The first fluorophore and the second fluorophore can comprise a fluorescence resonance energy transfer (FRET) pair. The second fluorophore can disassociate from the first fluorophore, thereby generating a change in maximum emission wavelength. The second fluorophore can disassociate from the first fluorophore at a rate selected such that the change in maximum emission wavelength indicates a predetermined period of time has elapsed since the article has been removed from the receptacle.

If desired, the indicator can be suitable packaged so as to remain responsive to a change in a concentration of the trigger when disposed on or within the article. In some embodiments, the indicator can be encapsulated within an optically transparent tablet. The tablet can be formed from a porous polymer membrane formed from a thermoplastic polymer having $T_g$ greater than 121° C. The porous polymer membrane can have a pore size large enough to permit transmembrane permeation of the trigger while prohibiting transmembrane permeation of the indicator. A suitable membrane can be selected in view of the identity of the trigger and the identity of the indicator. For example, in embodiments where the indicator comprises a population of nanoparticles stabilized by a capping agent, and porous polymer membrane can have a pore size larger than the capping agent but smaller than the average particle size of the population of nanoparticles. In some examples, the porous polymer membrane can have a pore size of from 5 nm to 75 nm.

In some embodiments, the article comprises a medical device or an ophthalmic device, such as contact lens. In some embodiments, the indicator can be stable to autoclaving.

BRIEF DESCRIPTION OF THE DRAWINGS

FIGS. 5A and 5B demonstrate that indicator is inactive in the presence of capping agent in the external solution (e.g., while the indicator or article remaining in the receptacle) for red (FIG. 5A) and blue (FIG. 5B) color-changing single-particle systems.

FIG. 6 demonstrates color-retaining particles. The capping agent remains bound to color-retaining particles, including in the absence of capping agent in the external solution, such that color-retaining particles provide a constant background for color-to-color transitions.

FIG. 7 is a demonstration of color-to-color (purple-to-red) transition using a two-particle system (blue color-losing particle [programmed for 8 hours]+color-retaining red particle).

FIG. 8A shows schematic representations of a formed and sealed micropouch (left) and the two layers of porous polymer sandwiching the enclosed indicators. FIGS. 8B to 8D show schematic representation of the side-view of a sealed micropouch filled with solid blue (FIG. 8B), a ring of red (FIG. 8C) and solid red (FIG. 8D) indicators integrated into a contact lens (left) and images of such an integrated lens (right). FIGS. 8E to 8F are images of red (FIG. 8E) and purple (FIG. 8F) indicators before and after autoclaving to show stability against autoclaving. Two replicate samples filled with red indicator are shown in (FIG. 8E). (G) FIG. 8G shows immersion of red indicators against the respective solutions or PureMoist cleaning solution for up to 35 days show stability against them.

DETAILED DESCRIPTION

Figure 1A:
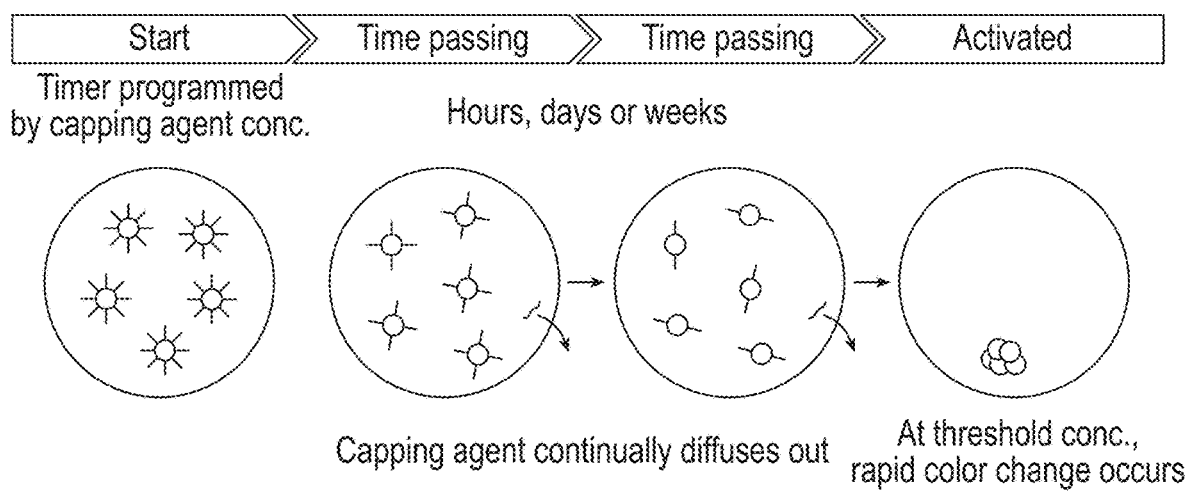
FIG. 1A is a schematic representation of the mechanism of action of one embodiment to indicate time elapsed based on a triggering event.

It is to be understood that the invention is not limited to the details of construction or process steps set forth in the following description. The invention is capable of other embodiments and of being practiced or being carried out in various ways using the teaching herein.

Definitions

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

The term "individual" includes humans and vertebrates.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light blocking, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The ophthalmic devices and lenses described herein may be comprised of silicone hydrogels or conventional hydrogels. Silicone hydrogels typically include at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result, and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495, 313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, falcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

The terms "reactive mixture" and "reactive monomer mixture" refer to the mixture of components (both reactive and non-reactive) which are mixed together and when subjected to polymerization conditions form the conventional or silicone hydrogels of the present invention as well as contact lenses made therefrom. The reactive monomer mixture may comprise reactive components such as the monomers, macromers, prepolymers, cross-linkers, and initiators, additives such as wetting agents, release agents, polymers, dyes, light absorbing compounds such as UV absorbers, pigments, dyes and photochromic compounds, any of which may be reactive or non-reactive but are capable of being retained within the resulting biomedical device, as well as pharmaceutical and nutraceutical compounds, and any diluents. It will be appreciated that a wide range of additives may be added based upon the biomedical device which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a hydrogel contact lens comprising at least one silicone containing component. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

As used herein, the term "alkyl" refers to an unsubstituted or substituted linear or branched alkyl group containing the indicated number of carbon atoms. If no number is indicated, then alkyl (optionally including any substituents on alkyl) may contain 1 to 16 carbon atoms. Preferably, the alkyl group contains 1 to 10 carbon atoms, alternatively 1 to 7 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, amido, carbamate, carbonate, halogen, phenyl, benzyl, and combinations thereof. "Alkylene" means a divalent alkyl group, such as —CH$_2$—, —CH$_2$CH$_2$—, —CH$_2$CH$_2$CH$_2$—, —CH$_2$CH(CH$_3$)CH$_2$—, and —CH$_2$CH$_2$CH$_2$CH$_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —CF$_3$— or —CF$_2$CF$_3$—. "Haloalkylene" means a divalent haloalkyl group, such as —CH$_2$CF$_2$—.

"Cycloalkyl" refers to an unsubstituted or substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an unsubstituted or substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, amido, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —$CH_2CH_2NH$—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R_3Si$— and "siloxy" refers to a structure of formula $R_3Si$—O—, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[$CH_2CH_2O$]$_p$— or $CH_3O$—[$CH_2CH_2O$]$_p$—). Examples of alkyleneoxy include polymethyleneoxy, polyethyleneoxy, polypropyleneoxy, polybutyleneoxy, and poly(ethyleneoxy-co-propyleneoxy).

"Oxaalkylene" refers to an alkylene group as defined above where one or more non-adjacent $CH_2$ groups have been substituted with an oxygen atom, such as —$CH_2CH_2OCH(CH_3)CH_2$—. "Thiaalkylene" refers to an alkylene group as defined above where one or more non-adjacent $CH_2$ groups have been substituted with a sulfur atom, such as —$CH_2CH_2SCH(CH_3)CH_2$—.

The term "linking group" refers to a moiety that links the polymerizable group to the parent molecule. The linking group may be any moiety that does not undesirably interfere with the polymerization of the compound of which it is a part. For instance, the linking group may be a bond, or it may comprise one or more alkylene, haloalkylene, amide, amine, alkyleneamine, carbamate, carboxylate (—$CO_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —$OCF_2$—, —$OCF_2CF_2$—, —$OCF_2CH_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, $CH_3O$-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include $C_1$-$C_8$ alkylene (preferably $C_2$-$C_6$ alkylene) and $C_1$-$C_8$ oxaalkylene (preferably $C_2$-$C_6$ oxaalkylene), each of which is optionally substituted with 1 or 2 groups independently selected from hydroxyl and siloxy. Preferred linking groups also include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties as described above (e.g., alkylene and cycloalkylene), the moieties may be present in any order. For instance, if in Formula E below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg) to which the linking group is attached. For example, if in Formula E, L and $L^2$ are indicated as both being alkylene-cycloalkylene, then Rg-L is preferably Rg-alkylene-cycloalkylene- and -$L^2$-Rg is preferably -cycloalkylene-alkylene-Rg.

"Nanoparticle" as used herein refers to a microscopic particle having at least one dimension that is less than 100 nm. In some cases, nanoparticles can have at least one dimension less than 50 nm. "Plasmonic nanoparticle" as used herein refers to a metal nanoparticle that has a strong absorption (and scattering) spectrum that is tunable by changing the shape, the composition or the medium around the particle surface. It will be appreciated that the term includes all plasmonic nanoparticles of various shapes that gives rise to a surface plasmon absorption and scattering spectrum in the blue region of the electromagnetic spectrum (e.g., between 400 nm and 500 nm).

"Surface plasmon" or "surface plasmon resonance" as used herein refers to resonant oscillations of oscillating electric fields of a ray of light propagating near a colloidal nanoparticle that interact with the free electrons thus causing an oscillation of electron charge that is in resonance with the frequency of visible light.

As used herein, "optical indicator" means any desired substance that may be used, that is reducible, and that upon reduction undergoes a visually detectable and/or machine-detectable change in the optical properties thereof, such as color, fluorescence, emission, transmission, polarization, and/or refractive index. Examples of observable changes include changes in absorption wavelength (e.g., changes in color), changes in emission wavelength, changes in fluorescence lifetime, and changes in fluorescence quantum yield. Changes in fluorescence quantum yield can include a decrease in fluorescence intensity (termed "quenching") or an increase in fluorescence intensity.

The phrase "visible indicator," as used herein, refers to an optical indicator which undergoes a visually detectable and/or machine-detectable change in an optical property within the visible region of the electromagnetic spectrum (e.g., at a wavelength of from 350 nm to 750 nm).

The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects.

The term "static concentration", as used herein, refers to a concentration of the trigger, which may vary from about 1% to about 10%. For example, the static concentration may vary by +/−10%, +/−5%, +/−2%, or +/−1%.

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

Systems

Provided herein are systems and methods which can be used to indicate the period of time elapsed since the occurrence of a triggering event. More particularly, this application relates to systems and methods which can be used to visually indicate, for example, the time period elapsed since an article has been removed from its packaging, the period of time elapsed since an article or composition has been prepared, and/or the period of time that an article has been in use.

The system can include an indicator disposed on or within the article. The article may be enclosed within a sealable receptacle of a package. The system can further include a trigger disposed within the receptacle and in contact with the indicator. The indicator can be responsive to a change in a concentration of the trigger in contact with the indicator. As discussed in more detail below, the indicator can comprise a nanoparticle, chromophore or a fluorophore or a combination thereof. The trigger can comprise a capping agent, a dispersant, a quencher, a second fluorophore, or a combination thereof.

The trigger can be present in the sealable receptacle at a static concentration. For example, in some embodiments, the concentration of trigger can vary by less than +/−10% (e.g., less than +/−5%, less than +/−2%, or less than +/−1%) from the time the article is enclosed within the sealable receptacle to the time the article is removed from the sealable receptacle.

Removal of the article from the sealable receptacle can induce a change in concentration of the trigger in contact with the indicator. A change in the concentration of the trigger can induce an observable change in the indicator. For example, in some embodiments, the indicator can be an optical indicator (e.g., a visible indicator) in which the observable change comprises a change in the color of the indicator. In such cases, the observable change can be a change in color from a first color in the visible spectrum to a second color in the visible spectrum; a change in color from a first color outside of the visible spectrum to a second color in the visible spectrum; or a change in color from a first color in the visible spectrum to a second color outside of the visible spectrum. The observable change (e.g., the color change) can indicate that a predetermined period of time has elapsed since the article has been removed from the receptacle. In some embodiments, the predetermined period of time can be from 30 minutes to 30 days, such as from 1 hour to 30 days. For example, the predetermined period of time can be from 24 hours to 30 days, from 1 hour to 15 days, or from 24 hours to 15 days.

Importantly, the observable change can be discrete, such that substantially all of the observable change (e.g., the color change) occurs at the predetermined period of time. For example, substantially no observable change can occur prior to the predetermined period of time. Then, the observable change can occur within a relatively short period of time at and following the predetermined period of time. For example, substantially all of the observable change can occur within 48 hours (e.g., within 24 hours, within 12 hours, within 6 hours, within 5 hours, within 4 hours, within 3 hours, within 2 hours, within 1 hour, or within 30 minutes) of the predetermined period of time.

In some embodiments, a change in the concentration of the trigger can induce two or more observable changes in this indicator, so as to indicate two or more predetermined periods of time have elapsed since the article has been removed from the receptacle. In some embodiments, the first predetermined period of time can be from 10 minutes to two weeks and wherein the second predetermined period of time is from 30 minutes to 30 days, such as from 1 hour to 30 days. For example the first predetermined period of time can be from 15 minutes to two weeks, from 30 minutes to two weeks, from 1 hour to two weeks, from 1 hour to 24 hours, from 1 hour to one week, from 30 minutes to one week, or from 10 minutes to 24 hours, and the second predetermined period of time can be from 1 hour to 30 days, from 24 hours to 30 days, from 1 hour to 15 days, or from 24 hours to 15 days.

Nanoparticle Indicators

In some embodiments, the indicator can comprise a population of nanoparticles stabilized by a capping agent. In these the trigger comprises a solution comprising the capping agent in contact with the indicator.

The concentration of the capping agent in the trigger can comprise an equilibrium concentration of the capping agent. When the article is removed from the receptacle and placed in contact with a solution containing a lower concentration of the trigger, the capping agent disassociates from the nanoparticles, thereby inducing aggregation of the population of nanoparticles. This aggregation results in a color change.

The capping agent disassociates from the nanoparticles at a rate selected (by virtue of selecting an appropriate capping agent) such that the color change indicates a predetermined period of time has elapsed since the article has been removed from the receptacle. In some embodiments, the predetermined period of time is from 1 hour to 30 days. For example, the predetermined period of time can be from 24 hours to 30 days, from 1 hour to 15 days, or from 24 hours to 15 days. The color change can be observed (e.g., visually and/or spectroscopically) by a user of the article to determine when a predetermined period of time has elapsed since the article has been removed from the receptacle.

In desired, multiple populations of nanoparticles stabilized by capping agents can be combined in a single indicator so as to provide multiple observable indications of the time elapsed since an article has been removed from its receptacle. By way of example, in some embodiments, the indicator can comprise a first population of nanoparticles stabilized by a first capping agent and a second population of nanoparticles stabilized by a second capping agent. The trigger can comprise a solution comprising the first capping agent and the second capping in contact with the indicator. In these embodiments, when the article is removed from the receptacle and placed in contact with a solution containing a lower concentration of the trigger, the first capping agent disassociates from first population of nanoparticles at a different rate (e.g., a faster rate) than the second capping agent disassociates from the second population of nanoparticles. When the article is removed from the receptacle and placed in contact with a solution containing a lower concentration of the trigger, the first capping agent can disassociate from the first population nanoparticles, thereby inducing aggregation of the first population of nanoparticles and generating a first color change. Subsequently, the second capping agent can disassociate from the second population nanoparticles, thereby inducing aggregation of the second population of nanoparticles and generating a second color change.

The first capping agent can disassociate from the first population of nanoparticles at a first rate selected (by virtue of selecting an appropriate capping agent) such that the first color change indicates a first predetermined period of time has elapsed since the article has been removed from the receptacle. Likewise, the second capping agent can disassociate from the second population nanoparticles at a second rate selected (by virtue of selecting an appropriate capping agent) such that the second color change indicates a second predetermined period of time has elapsed since the article has been removed from the receptacle. In some embodiments, the first predetermined period of time can be from 10 minutes to two weeks, from 15 minutes to two weeks, from 30 minutes to two weeks, from 1 hour to two weeks, from 1 hour to 24 hours, from 1 hour to one week, from 30 minutes to one week, or from 10 minutes to 24 hours and the second predetermined period of time can be from 1 hour to 30 days, from 24 hours to 30 days, from 1 hour to 15 days, or from 24 hours to 15 days.

In some embodiments, nanoparticles can comprise plasmonic nanoparticles. The plasmonic nanoparticle can comprise any suitable noble metal (e.g., gold, silver, platinum, palladium, or any combination thereof). In some embodiments, the nanoparticles can comprise gold. In certain embodiments, the nanoparticles can consist of gold. In some embodiments, the nanoparticles can comprise silver. In certain embodiments, the nanoparticles can consist of silver.

The size and shape of the nanoparticle can be varied to tune the optical properties of the nanoparticles. For example, by varying the size and shape of the nanoparticles, the absorption of the nanoparticles can be tuned across a wide range of wavelengths. The nanoparticles can have any suitable shape, such as a cage, cone, cylinder, cube, cuboid, hexagon, icosahedra, octahedra, plate, prism, pyramid, ring, rod, shell, sphere, star, tetrahedra, etc.

In some embodiments, the nanoparticles can have a polyhedral shape. For example, the nanoparticles can have a cubic shape, an octahedral shape, a decahedral shape, a cuboctahedral shape, a tetrahedral shape, a rhombic dodecahedral shape, a truncated ditetragonal prismatic shape, or a truncated bitetrahedral shape. In other embodiments, nanoparticles can have a spherical shape. In other embodiments, nanoparticles can comprise rods.

In some cases, the population of nanoparticles can have a homogenous particle shape. In these embodiments, substantially all of the nanoparticles (e.g., at least 90%, at least 95%, or at least 98% of the nanoparticless) can have the same particle shape. In other cases, the population of nanoparticles can comprise a mixture of particle shapes (e.g., a mixture of two, three, four, five, six, seven, or more different particle shapes with the population of nanoparticles). For example, in some examples, the nanoparticles comprise a first population of nanoparticles having a first shape and a second population of nanoparticles having a second shape.

The population of nanoparticles can have an average particle size. "Average particle size" and "mean particle size" are used interchangeably herein, and generally refer to the statistical mean particle size of the nanoparticles in a population of nanoparticles. For a nanoparticle with a substantially spherical shape, the diameter of a nanoparticle can refer, for example, to the hydrodynamic diameter. As used herein, the hydrodynamic diameter of a particle can refer to the largest linear distance between two points on the surface of the particle. For nanoparticle cores having non-spherical shapes, the diameter of a nanoparticle can refer, for example, to the smallest cross-sectional dimension of the nanoparticle (i.e., the smallest linear distance passing through the center of the nanoparticle and intersecting two points on the surface of the particle). Mean particle size can be measured using methods known in the art, such as evaluation by scanning electron microscopy, transmission electron microscopy, and/or dynamic light scattering.

In some embodiments, the nanoparticles can have an average particle size of at least 5 nm (e.g., at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, or at least 95 nm), as measured by transmission electron microscopy (TEM). In some embodiments, the nanoparticles can have an average particle size of 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 15 nm or less, or 10 nm or less), as measured by transmission electron microscopy (TEM).

The nanoparticles can have an average particle size ranging from any of the minimum values described above to any of the maximum values described above. For example, in some embodiments, the nanoparticles can have an average particle size of from 5 nm to 100 nm (e.g., from 20 nm to 60 nm), as measured by transmission electron microscopy (TEM).

In some cases, the nanoparticles can have a monodisperse particle size distribution. "Monodisperse" and "homogeneous size distribution," as used herein, and generally describe a population of particles where all of the particles are the same or nearly the same size. As used herein, a monodisperse distribution refers to particle distributions in which 80% of the distribution (e.g., 85% of the distribution, 90% of the distribution, or 95% of the distribution) lies within 25% of the mean particle size (e.g., within 20% of the mean particle size, within 15% of the mean particle size, within 10% of the mean particle size, or within 5% of the mean particle size). In other cases, the nanoparticles can have a polydisperse or heterogeneous particle size distribution.

In some embodiments, the nanoparticles can exhibit a maximum absorption value of at least 450 nm (e.g., at least 475 nm, at least 500 nm, at least 525 nm, at least 550 nm, at least 575 nm, at least 600 nm, at least 625 nm, at least 650 nm, at least 675 nm, at least 700 nm, or at least 725 nm). In some embodiments, the nanoparticles can exhibit a maximum absorption value of 750 nm or less (e.g., 725 nm or less, 700 nm or less, 675 nm or less, 650 nm or less, 625 nm or less, 600 nm or less, 575 nm or less, 550 nm or less, 525 nm or less, 500 nm or less, or 475 nm or less).

The nanoparticles can exhibit a maximum absorption value ranging from any of the minimum values described above to any of the maximum values described above. For example, in some embodiments, the nanoparticles can exhibit a maximum absorption value of from 450 nm to 750 nm (e.g., from 450 nm to 500 nm, from 500 nm to 550 nm, from 550 nm to 600 nm, from 600 nm to 650 nm, from 650 nm to 700 nm, or from 700 nm to 750 nm).

In some embodiments, the nanoparticles can exhibit an absorption spectrum having a full-width at half maximum of at least 20 nm (e.g., at least 25 nm, at least 30 nm, at least 35 nm, at least 40 nm, at least 45 nm, at least 50 nm, at least 55 nm, at least 60 nm, at least 65 nm, or at least 70 nm). In some embodiments, the nanoparticles can exhibit an absorption spectrum having a full-width at half maximum of 75 nm or less (e.g., 70 nm or less, 65 nm or less, 60 nm or less, 55 nm or less, 50 nm or less, 45 nm or less, 40 nm or less, 35 nm or less, 30 nm or less, or 25 nm or less).

The nanoparticles can exhibit an absorption spectrum having a full-width at half maximum ranging from any of the minimum values described above to any of the maximum values described above. For example, in some embodiments, the core-shell particles can exhibit an absorption spectrum having a full-width at half maximum of from 20 nm to 75 nm.

The capping agent can comprise any suitable agent which stabilizes the nanoparticles, such that aggregation of the nanoparticles is minimized when the capping agent is associated with the nanoparticles. The capping agent can be non-covalently (ionically) associated with the nanoparticles.

In some embodiments, the capping agent can be biocompatible. This is particularly preferred in embodiments where the article is intended to be in contact with a living organism.

Examples of suitable capping agents include, for example, surfactants, polymers, and combinations thereof. Representative examples of capping agents include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthlate, noncrystalline cellulose, magnesium aluminum silicate, triethanolamine, polyvinyl alcohol, and polyvinylpyrrolidone (PVP). Most of these capping agents are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Specific examples of capping agents include polyvinylpyrrolidone, tyloxapol, poloxamers such as Pluronic™ F68 and F108, which are block copolymers of ethylene oxide and propylene oxide, and poloxamines such as Tetronic™ 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT™, which is a dioctyl ester of sodium sulfosuccinic acid, available from American Cyanimid, Duponol™ P, which is a sodium lauryl sulfate, available from DuPont, Triton™ X-200, which is an alkyl aryl polyether sulfonate, available from Rohm and Haas, Tween 80, which is a polyoxyethylene sorbitan fatty acid ester, available from ICI Specialty Chemicals, and Carbowax™ 3350 and 934, which are polyethylene glycols available from Union Carbide. Other useful capping agents include: decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, and the like.

In certain embodiments, the capping agent comprises a surfactant, such as an anionic surfactant, a cationic surfactant, a non-ionic surfactant, an amphoteric surfactant, or a combination thereof. In some examples, the surfactant can comprise a phosphatide such as lecithin, a polyoxyethylene sorbitan fatty acid ester, a polyoxyethylene alkyl ether, stearic acid, benzalkonium chloride, calcium stearate, glycerol monostearate, cetostearyl alcohol, 3-[N,N-Dimethyl(3-palmitoylaminopropyl)ammonio]-propanesulfonate, N-Dodecyl-N,N-(dimethylammonio)butyrate, sodium dodecyl sulfate (SDS), sodium lauryl sulfate, octadecanoic acid, a poloxamer, a poloxamine, an alkyl aryl polyether sulfonate, palmitic acid, dodecylphosphonic acid, sodium oleate, sodium octanoate, cetyltrimethylammonium bromide, tetrabutylammonium hydroxide titrant, sodium dodecyl phosphonate, tetrabutylammonium palmitate, tetrabutylammonium laurate, a polysorbate, or a combination thereof.

In certain embodiments, the capping agent comprises a polymer, such as polyvinylpyrrolidone, polyvinyl alcohol, a polyalkylene oxide such as a polyethylene glycol, a cellulosic polymer, tyloxapol, or a combination thereof.

In other embodiments, the indicators can be color-retaining indicators. The capping agent(s) of color-retaining indicators do not diffuse out of the receptacle. The capping agent(s) can be kept within the receptacle by having the receptacle have a MWCO below the molecular weight of a color-retaining capping agent. In another embodiment, the capping agent can associate strongly to its indicator such that there is insignificant net diffusion of the capping agent out of the receptacle.

Fluorophore Indicators

In other embodiments, the indicator can comprise a fluorophore in combination with a dispersant, and the trigger can comprise a solution comprising the dispersant in contact with the indicator. In some embodiments, when the article is removed from the receptacle and placed in contact with a solution containing a lower concentration of the trigger, the dispersant disassociates from the fluorophore, thereby inducing aggregation of the fluorophore and generating a change (e.g., a red shift) in maximum emission wavelength.

The dispersant can disassociate from the fluorophore at a rate selected such that the change in fluorescence of the fluorophore indicates a predetermined period of time has elapsed since the article has been removed from the receptacle. The change in fluorescence can comprise a change in maximum emission wavelength, a change in fluorescence quantum yield, a change in a shape of an emission spectra, a change in fluorescence lifetime, or a combination thereof.

In other embodiments, the indicator can comprise a fluorophore, and the trigger can comprise a solution including the quencher in contact with the indicator. In some embodiments, when the article is removed from the receptacle and placed in contact with a solution containing a lower concentration of the trigger, the quencher can disassociate from the fluorophore, thereby inducing an increase in fluorescence. The quencher can disassociate from the fluorophore at a rate selected such that the increase in fluorescence indicates a predetermined period of time has elapsed since the article has been removed from the receptacle.

In other embodiments, the indicator can comprise a first fluorophore, and the trigger can comprise a solution including a second fluorophore in contact with the indicator. The first fluorophore and the second fluorophore can comprise a fluorescence resonance energy transfer (FRET) pair. The second fluorophore can disassociate from the first fluorophore, thereby generating a change in maximum emission wavelength. The second fluorophore can disassociate from the first fluorophore at a rate selected such that the change in maximum emission wavelength indicates a predetermined period of time has elapsed since the article has been removed from the receptacle.

The fluorophore can be selected to possess photophysical properties which facilitate the observation and/or analysis of the spectroscopic properties of the fluorophore. For example, in certain embodiments, the fluorophore possesses a fluorescence quantum yield that facilitates observation and/or measurement of the indicator's fluorescence. In some cases, the fluorophore possesses a quantum yield of at least 0.10, 0.15, 0.20, 0.25, 0.30, 0.35, 0.40, 0.45, 0.50, 0.55, 0.60, 0.65, 0.70, 0.75, 0.80, 0.85, or 0.90 in aqueous solution.

In some cases, the fluorophore does not possess an emission maximum in a spectral region which substantially overlaps with the autofluorescence of biological samples. In certain embodiments, the fluorophore possesses an emission maximum greater than 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, or 700 nm in aqueous solution. In certain embodiments, the fluorophore possesses an emission maximum in aqueous solution between 430 nm and 700 nm, more preferably between 450 nm and 700 nm, most preferably between 480 nm and 700 nm. In some embodiments, the fluorophore possesses an emission maximum in aqueous solution between 430 nm and 1200 nm, more preferably between 450 nm and 1200 nm, most preferably between 480 nm and 1200 nm.

In preferred embodiments, the fluorophore is selected to possess the photophysical properties, including fluorescence quantum yield and emission maxima, which are observable by the naked eye when the indicator (e.g., the article comprising the indicator) is irradiated with UV light. In some embodiments, the fluorophore possesses a high quantum yield and emits at a long wavelength. In a particular embodiment, the fluorophore possesses an emission maximum greater than 450 nm and a quantum yield of greater than 0.10 in aqueous solution.

A variety of suitable fluorophore may be used as indicators. Fluorophores useful as indicators typically contain an extended conjugation path (e.g., alternating single and double bonds) over which pi electrons are delocalized. The fluorophore can be aromatic, meaning it contains one or more aromatic rings, or non-aromatic (e.g., a linear structure). In preferred embodiments, the fluorophore contains one or more aromatic rings.

In some embodiments, the fluorophore is an organic or organometallic small molecule. Suitable small molecule fluorophores are known in the art, and include, but are not limited to, xanthene and xanthene derivatives, such as fluorescein or a fluorescein derivative, rhodamine, Oregon green, eosin, Texas red, and Cal Fluor dyes; cyanine and cyanine derivatives, such as indocarbocyanine, oxacarbocyanine, thiacarbocyanine, merocyanine, and Quasar dyes; naphthalene derivatives, such as dansyl and prodan derivatives and naphthalimide and naphthalimide derivatives; coumarin and derivatives thereof; oxadiazole derivatives, such as pyridyloxazole, nitrobenzoxadiazole and benzoxadiazole; pyrene derivatives, such as cascade blue; oxazine derivatives, such as Nile red, Nile blue, cresyl violet, and oxazine 170; acridine derivatives; such as proflavin, acridine orange, and acridine yellow; arylmethine derivatives, such as auramine, crystal violet, and malachite green; tetrapyrrole derivatives, such as porphin, phtalocyanine, and bilirubin; fluorene derivatives; CF® dye (available from Biotium); BODIPY® (available from Invitrogen); Alexa Fluor® (available from Invitrogen); DyLight Fluor® (available from Thermo Scientific); Atto® and Tracy® available from Sigma Aldrich; and FluoProbes® (available from Interchim). Other suitable fluorophores include those described in Lakowicz, J. R. "Principles of Fluorescence Spectroscopy", $2^{nd}$ Ed., Plenum Press, New York, 1999.

Suitable fluorophores can also include macromolecules, such as conjugated polymers. In some embodiments, the fluorophore is a conjugated polymer, such as a poly(arylene ethynylene), containing one or more sidechains that contain reactive functional groups.

Other suitable fluorophores include any substance which can absorb energy of an appropriate wavelength and emit or transfer energy. Typical fluorophores include fluorescent dyes, semiconductor nanocrystals, lanthanide chelates, and fluorescent protein.

Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-$Br_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates. Exemplary fluorescent proteins (FPs) include green fluorescent protein (GFP), red fluorescent protein (RFP), yellow fluorescent protein (YFP), cyan fluorescent protein (CFP), dark FPs, large strokes shift FPs, far red FPs, and infrared FPs.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

In some embodiments, suitable fluorophores can be metal chalcogenide quantum dots, graphene quantum dots, carbon dots, graphite oxide, semiconducting (organic) polymer dots, ultrasmall metallic nanoparticles (e.g., gold or silver), metal nanoclusters (e.g., gold, silver, copper), fluorescently doped silica nanoparticles, fluorescently doped silica microparticles, fluorophore-functionalized dendrimers, and upconversion nanoparticles or combinations thereof.

As discussed above, in some examples, the indicator can comprise a fluorophore in combination with a dispersant. The dispersant can include any suitable agent which stabilizes the fluorophore, such that aggregation of the fluorophore is minimized in the presence of the dispersant. In some embodiments, the dispersant can be biocompatible. This is particularly preferred in embodiments where the article is intended to be in contact with a living organism.

Examples of suitable dispersant include, for example, surfactants, polymers, and combinations thereof. Representative examples of dispersant include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthlate, noncrystalline cellulose, magnesium aluminum silicate, triethanolamine, polyvinyl alcohol, and polyvinylpyrrolidone (PVP). Most of these dispersant are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Specific examples of dispersant include polyvinylpyrrolidone, tyloxapol, poloxamers such as Pluronic™ F68 and F108, which are block copolymers of ethylene oxide and propylene oxide, and poloxamines such as Tetronic™ 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT™, which is a dioctyl ester of sodium sulfosuccinic acid, available from American Cyanimid, Duponol™ P, which is a sodium lauryl sulfate, available from DuPont, Triton™ X-200, which is an alkyl aryl polyether sulfonate, available from Rohm and Haas, Tween 80, which is a polyoxyethylene sorbitan fatty acid ester, available from ICI Specialty Chemicals, and Carbowax™ 3350 and 934, which are polyethylene glycols available from Union Carbide. Other useful surface modifiers include: decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, and the like.

In certain embodiments, the dispersant comprises a surfactant, such as an anionic surfactant, a cationic surfactant, a non-ionic surfactant, an amphoteric surfactant, or a combination thereof. In some examples, the dispersant can comprise a phosphatide such as lecithin, a polyoxyethylene sorbitan fatty acid ester, a polyoxyethylene alkyl ether, stearic acid, benzalkonium chloride, calcium stearate, glycerol monostearate, cetostearyl alcohol, 3-[N,N-Dimethyl(3-palmitoylaminopropyl)ammonio]-propanesulfonate, N-Dodecyl-N,N-(dimethylammonio)butyrate, sodium dodecyl sulfate (SDS), sodium lauryl sulfate, octadecanoic acid, a poloxamer, a poloxamine, an alkyl aryl polyether sulfonate, palmitic acid, dodecylphosphonic acid, sodium oleate, sodium octanoate, cetyltrimethylammonium bromide, tetrabutylammonium hydroxide titrant, sodium dodecyl phosphonate, tetrabutylammonium palmitate, tetrabutylammonium laurate, a polysorbate, or a combination thereof.

In certain embodiments, the dispersant comprises a polymer, such as polyvinylpyrrolidone, polyvinyl alcohol, a polyalkylene oxide such as a polyethylene glycol, a cellulosic polymer, tyloxapol, or a combination thereof.

As discussed above, in other examples, the indicator can comprise a fluorophore, and the trigger can comprise a solution including the quencher in contact with the indicator. The term "quencher" refers to a substance or portion thereof which is capable of suppressing, reducing, inhibiting, etc., the detectable fluorescence produced by the fluorophore. Suitable quenchers may be selected in view of the identity of the fluorophore. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™ each of which are available from Biosearch Technologies, Inc. of Novato, Calif., QSY-7™ QSY-9™, QSY-21™ and QSY-35™, each of which are available from Molecular Probes, Inc., and the like, metallic nanoparticles (e.g., gold, silver, copper), graphene oxide, iron oxide nanoparticles, metal-organic frameworks, carbon nanoparticles, and quantum dots (QDs), or combinations thereof.

As discussed above, in other examples, the indicator can comprise a first fluorophore, and the trigger can comprise a solution including a second fluorophore in contact with the indicator. The first fluorophore and the second fluorophore can comprise a FRET pair. In such pairs, when the first fluorophore and the second fluorophore are in close proximity, and the first fluorophore is excited by an energy source, a substantial portion of the energy of the excited state nonradiatively transfers to the second fluorophore where it either dissipates nonradiatively or is emitted at a different emission wavelength than that of the first fluorophore.

Suitable FRET pairs are known in the art, and can include small organic dyes, fluorescent proteins, metallic nanoparticles (e.g., gold, silver, copper), graphene oxide, iron oxide nanoparticles, metal-organic frameworks, carbon nanoparticles, and quantum dots (QDs) or combinations thereof. Exemplary FRET pairs include dansyl-rhodamine, naphthalene-pyrene, Green FP-Red FP, Cyan FP-Yellow FP, CdSe/ZnS QD, or CdSe/ZnS QD-Red FP.

Chromophore Indicators

In other embodiments, the indicator can comprise a chromophore in combination with a dispersant. A wide variety of chromophores are known in the art. Examples of suitable chromophores include molecules that possess extensive delocalized electron systems, such as cyanines, merocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline complexes, bis(S,O-dithiolene) complexes and the like.

Examples of chromophores, which may be used, include xylene cyanole, fluorescein, dansyl, NBD, indocyanine green, DODCI, DTDCI, DOTCI and DDTCI. Additional examples of organic chromophores include, but are not limited to, cyanine dyes, chalcogenopyrylomethine dyes, pyrilium dyes, thiapyrilium dyes, squarylium dyes, croconium dyes, azulenium dyes, merocyanine dyes, indoaniline dyes including Cu and Ni complexes, indanthrene pigments, trisphenoquinone dyes, azo dyes, non-benzenoid aromatic dyes, tetrazine radical dyes, anthraquinone dyes, naphthoquinone dyes, metallated azo dyes including those containing Ni, Co, Fe and Mn, phthalocyanine dyes, naphthalocyanine dyes, metal phthalocyanines, metal naphthalocyanines, bis(dithiolene) metal complexes, bis(benzenedithiolate) metal complexes, bis(S,O-dithiolene) metal complexes, and tris(a-diimine) metal complexes. Representative examples are found in U.S. Pat. No. 6,051,207, which is incorporated herein in its entirety.

In some embodiments, the chromophore can comprise a visible dye. Examples of visible dyes include, but are not limited to, fluorescein dyes, rhodamine dyes, coumarins, azo dyes, metalizable dyes, anthraquinone dyes, benzodifuranone dyes, polycyclic aromatic carbonyl dyes, indigoid dyes, polymethine dyes, azacarbocyanine dyes, hemicyanine dyes, barbituates, diazahemicyanine dyes, stryrl dyes, diaryl carbonium dyes, triaryl carbonium dyes, phthalocyanine dyes, quinophthalone dyes, triphenodioxazine dyes, formazan dyes, phenothiazine dyes, such as methylene blue, azure A, azure B, and azure C, oxazine dyes, thiazine dyes, naphtholactam dyes, diazahemicyanine dyes, azopyridone dyes, azobenzene dyes, xanthene dyes, leuco dyes which can be oxidized to produce dyes with hues bathochromically shifted from those of the precursor leuco dyes, and any other visible dyes known in the art.

The dispersant can comprise any suitable agent which stabilizes the chromophore, such that aggregation of the chromophore is minimized in the presence of the dispersant. In some embodiments, the dispersant can be biocompatible. This is particularly preferred in embodiments where the article is intended to be in contact with a living organism.

Examples of suitable dispersant include, for example, surfactants, polymers, and combinations thereof. Representative examples of dispersant include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP). Most of these dispersant are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Specific examples of dispersant include polyvinylpyrrolidone, tyloxapol, poloxamers such as Pluronic™ F68 and F108, which are block copolymers of ethylene oxide and propylene oxide, and poloxamines such as Tetronic™ 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT™, which is a dioctyl ester of sodium sulfosuccinic acid, available from American Cyanimid, Duponol™ P, which is a sodium lauryl sulfate, available from DuPont, Triton™ X-200, which is an alkyl aryl polyether sulfonate, available from Rohm and Haas, Tween 80, which is a polyoxyethylene sorbitan fatty acid ester, available from ICI Specialty Chemicals, and Carbowax™ 3350 and 934, which are polyethylene glycols available from Union Carbide. Other useful surface modifiers include: decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, and the like.

In certain embodiments, the dispersant comprises a surfactant, such as an anionic surfactant, a cationic surfactant, a non-ionic surfactant, an amphoteric surfactant, or a combination thereof. In some examples, the dispersant can comprise a phosphatide such as lecithin, a polyoxyethylene sorbitan fatty acid ester, a polyoxyethylene alkyl ether, stearic acid, benzalkonium chloride, calcium stearate, glycerol monostearate, cetostearyl alcohol, 3-[N,N-Dimethyl(3-palmitoylaminopropyl)ammonio]-propanesulfonate, N-Dodecyl-N,N-(dimethylammonio)butyrate, sodium dodecyl sulfate (SDS), sodium lauryl sulfate, octadecanoic acid, a poloxamer, a poloxamine, an alkyl aryl polyether sulfonate, palmitic acid, dodecylphosphonic acid, sodium oleate, sodium octanoate, cetyltrimethylammonium bromide, tetrabutylammonium hydroxide titrant, sodium dodecyl phosphonate, tetrabutylammonium palmitate, tetrabutylammonium laurate, a polysorbate, or a combination thereof.

In certain embodiments, the dispersant comprises a polymer, such as polyvinylpyrrolidone, polyvinyl alcohol, a polyalkylene oxide such as a polyethylene glycol, a cellulosic polymer, tyloxapol, or a combination thereof.

In some embodiments, the dispersant can disassociate from the chromophore, thereby inducing aggregation of the chromophore and generating a color change.

Articles

The systems described herein can be applied to a variety of articles to provide a ready means of assessing the period of time that has elapsed since article has been removed from its packaging, the period of time elapsed since an article or composition has been prepared, and/or the period of time that an article has been in use.

The indicator can be uniformly disposed throughout the article or a region of the article. Alternatively, the indicator can be patterned on and/or within the indicator (e.g., in the form of letters, numbers, shapes, logos, etc.) to generate an article having region(s) that include an indicator and other region(s) that do not include an indicator. In some embodiments, the indicator can be present in a tablet disposed on and/or within the article, as discussed in more detail below.

In some embodiments, the article can comprise a medical device (e.g., a bandage, orthodontic devices, an implantable medical device). In some embodiments, the article can comprise an ophthalmic device (e.g., a contact lens, a corneal onlay, a corneal inlay, an intraocular lens, an overlay lenses, etc.). In certain embodiments, the ophthalmic device can comprise a contact lens, such as a hard contact lens or a soft contact lens. In these embodiments, the indicator can function as a compliance indicator, visually indicating when a desired time period has elapsed since the contact lens was removed from its packaging (and by extension when the contact lens needs to be replaced).

In some embodiments, the article can comprise hydrogel or silicone hydrogel material suitable for use in the formation of a soft contact lens. Such materials are known in the art and include Group 1—Low Water (<50% $H_2O$) Nonionic Hydrogel Polymers (e.g., tefilcon, tetrafilcon A, crofilcon, helfilcon A, helfilcon B, mafilcon, polymacon, hioxifilcon B); Group 2—High Water (>50% $H_2O$) Nonionic Hydrogel Polymers (e.g., surfilcon A, lidofilcon A, lidofilcon B, netrafilcon A, hefilcon B, alphafilcon A, omafilcon A, omafilcon B, vasurfilcon A, hioxifilcon A, hioxifilcon D, nelfilcon A, hilafilcon A, hilafilcon B, acofilcon A, nesofilcon A); Group 3—Low Water (<50% $H_2O$) Ionic Hydrogel Polymers (e.g., bufilcon A, deltafilcon A, phemfilcon); Group 4—High Water (>50% $H_2O$) Ionic Hydrogel Polymers (e.g., bufilcon A, perfilcon A, etafilcon A, focofilcon A, ocufilcon A, ocufilcon B, ocufilcon C, ocufilcon D, ocufilcon E, ocufilcon F, phemfilcon A, methafilcon A, methafilcon B, vilfilcon A); and Silicone Hydrogel Polymers (e.g., lotrafilcon A, lotrafilcon B, galyfilcon A, senofilcon A, senofilcon C, sifilcon A, comfilcon A, enfilcon A, balafilcon A, delefilcon A, narafilcon B, narafilcon A, stenfilcon A, somofilcon A, fanfilcon A, samfilcon A, elastofilcon).

In some embodiments, the article can comprise a silicone hydrogel. In certain embodiments, the article can comprise a polymer derived from polymerization of a reactive mixture that includes a hydrophilic monomer, a silicone-containing component, or combinations thereof. Example silicone hydrogel substrates include those discussed in detail below.

Hydrophilic Components

Examples of suitable families of hydrophilic monomers include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth) acrylamide, N-(3-hydroxybutyl) (meth)acrylamide, N-(4-hydroxybutyl) (meth)acrylamide, 2-aminoethyl (meth) acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth) acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-β-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl)amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and 3-((3-(methacryloyloxy)propyl) dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof Non-limiting examples of hydrophilic O-vinyl carbamates and O-vinyl carbonates monomers include N-2-hydroxyethyl vinyl carbamate and N-carboxy-ß-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of about 0.1 to about 80 weight percent, including in the range of about 5 to about 65 weight percent, and in the range of about 10 to about 45 weight percent, based on the total weight of the reactive components in the reactive monomer mixture.

Silicone-Containing Components

Silicone-containing components suitable for use comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, or mixtures of the foregoing; one or more optionally repeating siloxane units; and one or more linking groups connecting the polymerizable groups to the siloxane units.

Formula A. The silicone-containing component may comprise one or more polymerizable compounds of Formula A:

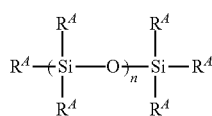

Formula A wherein:

at least one $R^A$ is a group of formula $R_g$-L- wherein $R_g$ is a polymerizable group and L is a linking group, and the remaining $R^A$ are each independently:

(a) $R_g$-L-,
(b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
(c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof,
(d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
(e) halo,
(f) alkoxy, cyclic alkoxy, or aryloxy,
(g) siloxy,
(h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or
(i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Formula B. The silicone-containing component of formula A may be a mono-functional polymerizable compound of formula B:

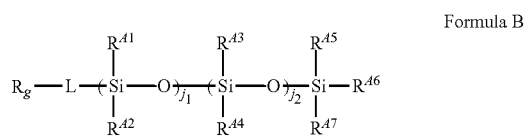

Formula B wherein:

Rg is a polymerizable group;

L is a linking group;

j1 and j2 are each independently whole numbers from 0 to 220, provided that the sum of j1 and j2 is from 1 to 220; $R^{A1}$, $R^{A2}$, $R^{A3}$, $R^{A4}$, $R^{A5}$, and $R^{A7}$ are independently at each occurrence $C_1$-$C_6$ alkyl, $C_3$-$C_{12}$ cycloalkyl, $C_1$-$C_6$ alkoxy, $C_4$-$C_{12}$ cyclic alkoxy, alkoxy-alkyleneoxy-alkyl, aryl (e.g., phenyl), aryl-alkyl (e.g., benzyl), haloalkyl (e.g., partially or fully fluorinated alkyl), siloxy, fluoro, or combinations thereof, wherein each alkyl in the foregoing groups is optionally substituted with one or more hydroxy, amino, amido, oxa, carboxy, alkyl carboxy, carbonyl, alkoxy, carbamate, carbonate, halo, phenyl, or benzyl, each cycloalkyl is optionally substituted with one or more alkyl, hydroxy, amino, amido, oxa, carbonyl, alkoxy, carbamate, carbonate, halo, phenyl, or benzyl and each aryl is optionally substituted with one or more alkyl, hydroxy, amino, amido, oxa, carboxy, alkyl carboxy, carbonyl, alkoxy, carbamate, carbonate, halo, phenyl, or benzyl; and $R^{46}$ is siloxy, $C_1$-$C_8$ alkyl (e.g., $C_1$-$C_4$ alkyl, or butyl, or methyl), or aryl (e.g., phenyl), wherein alkyl and aryl may optionally be substituted with one or more fluorine atoms.

Formula B-1. Compounds of formula B may include compounds of formula B-1, which are compounds of formula B wherein j1 is zero and j2 is from 1 to 220, or j2 is from 1 to 100, or j2 is from 1 to 50, or j2 is from 1 to 20, or j2 is from 1 to 5, or j2 is 1.

B-2. Compounds of formula B may include compounds of formula B-2, which are compounds of formula B wherein j1 and j2 are independently from 4 to 100, or from 4 to 20, or from 4 to 10, or from 24 to 100, or from 10 to 100.

B-3. Compounds of formulae B, B-1, and B-2 may include compounds of formula B-3, which are compounds of formula B, B-1, or B-2 wherein $R^{41}$, $R^{42}$, $R^{43}$, and $R^{44}$ are independently at each occurrence $C_1$-$C_6$ alkyl or siloxy. Preferred alkyl are $C_1$-$C_3$ alkyl, or more preferably, methyl. Preferred siloxy is trimethylsiloxy.

B-4. Compounds of formulae B, B-1, B-2, and B-3 may include compounds of formula B-4, which are compounds of formula B, B-1, B-2, or B-3 wherein $R^{45}$ and $R^{47}$ are independently alkoxy-alkyleneoxy-alkyl, preferably they are independently a methoxy capped polyethyleneoxyalkyl of formula $CH_3O$—$[CH_2CH_2O]_p$—$CH_2CH_2CH_2$, wherein p is a whole number from 1 to 50.

B-5. Compounds of formulae B, B-1, B-2, and B-3 may include compounds of formula B-5, which are compounds of formula B, B-1, B-2, or B-3 wherein $R^{45}$ and $R^{47}$ are independently siloxy, such as trimethylsiloxy.

B-6. Compounds of formulae B, B-1, B-2, and B-3 may include compounds of formula B-6, which are compounds of formula B, B-1, B-2, or B-3 wherein $R^{45}$ and $R^{47}$ are independently $C_1$-$C_6$ alkyl, alternatively $C_1$-$C_4$ alkyl, or alternatively, butyl or methyl.

B-7. Compounds of formulae B, B-1, B-2, B-3, B-4, B-5, and B-6 may include compounds of formula B-7, which are compounds of formula B, B-1, B-2, B-3, B-4, B-5, or B-6 wherein $R^{46}$ is $C_1$-$C_8$ alkyl, preferably $C_1$-$C_6$ alkyl, more preferably $C_1$-$C_4$ alkyl (for example methyl, ethyl, n-propyl, or n-butyl). More preferably $R^{46}$ is n-butyl.

B-8. Compounds of formulae B, B-1, B-2, B-3, B-4, B-5, B-6, and B-7, may include compounds of formula B-8, which are compounds of formula B, B-1, B-2, B-3, B-4, B-5, B-6, or B-7 wherein Rg comprises styryl, vinyl carbonate, vinyl ether, vinyl carbamate, N-vinyl lactam, N-vinylamide, (meth)acrylate, or (meth)acrylamide. Preferably, Rg comprises (meth)acrylate, (meth)acrylamide, or styryl. More preferably, Rg comprises (meth)acrylate or (meth)acrylamide.

When Rg is (meth)acrylamide, the nitrogen group may be substituted with $R^{49}$, wherein $R^{49}$ is H, $C_1$-$C_8$ alkyl (preferably $C_1$-$C_4$ alkyl, such as n-butyl, n-propyl, methyl or ethyl), or $C_3$-$C_8$ cycloalkyl (preferably $C_5$-$C_6$ cycloalkyl), wherein alkyl and cycloalkyl are optionally substituted with one or more groups independently selected from hydroxyl, amide, ether, silyl (e.g., trimethylsilyl), siloxy (e.g., trimethylsiloxy), alkyl-siloxanyl (where alkyl is itself optionally substituted with fluoro), aryl-siloxanyl (where aryl is itself optionally substituted with fluoro), and silyl-oxaalkylene- (where the oxaalkylene is itself optionally substituted with hydroxyl).

B-9. Compounds of formulae B, B-1, B-2, B-3, B-4, B-5, B-6, B-7, and B-8 may include compounds of formula B-9, which are compounds of formula B, B-1, B-2, B-3, B-4, B-5, B-6, B-7, or B-8 wherein the linking group comprises alkylene (preferably $C_1$-$C_4$ alkylene), cycloalkylene (preferably $C_5$-$C_6$ cycloalkylene), alkyleneoxy (preferably ethyleneoxy), haloalkyleneoxy (preferably haloethyleneoxy), amide, oxaalkylene (preferably containing 3 to 6 carbon atoms), siloxanyl, alkylenesiloxanyl, carbamate, alkyleneamine (preferably $C_1$-$C_6$ alkyleneamine), or combinations of two or more thereof, wherein the linking group is optionally substituted with one or more substituents independently selected from alkyl, hydroxyl, ether, amine, carbonyl, siloxy, and carbamate.

B-10. Compounds of formulae B, B-1, B-2, B-3, B-4, B-5, B-6, B-7, B-8, and B-9 may include compounds of formula B-10, which are compounds of formula B, B-1, B-2, B-3, B-4, B-5, B-6, B-7, B-8, or B-9 wherein the linking group is alkylene-siloxanyl-alkylene-alkyleneoxy-, or alkylene-siloxanyl-alkylene-[alkyleneoxy-alkylene-siloxanyl]$_q$-alkyleneoxy-, where q is from 1 to 50.

B-11. Compounds of formulae B, B-1, B-2, B-3, B-4, B-5, B-6, B-7, B-8, and B-9 may include compounds of formula B-11, which are compounds of formula B, B-1, B-2, B-3, B-4, B-5, B-6, B-7, B-8, or B-9 wherein the linking group is $C_1$-$C_6$ alkylene, preferably $C_1$-$C_3$ alkylene, more preferably n-propylene.

B-12. Compounds of formulae B, B-1, B-2, B-3, B-4, B-5, B-6, B-7, B-8, and B-9 may include compounds of formula B-12, which are compounds of formula B, B-1, B-2, B-3, B-4, B-5, B-6, B-7, B-8, or B-9 wherein the linking group is alkylene-carbamate-oxaalkylene. Preferably, the linking group is $CH_2CH_2N(H)$—$C(=O)$—$O$—$CH_2CH_2$—$O$—$CH_2CH_2CH_2$.

B-13. Compounds of formulae B, B-1, B-2, B-3, B-4, B-5, B-6, B-7, B-8, and B-9 may include compounds of formula B-13, which are compounds of formula B, B-1, B-2, B-3, B-4, B-5, B-6, B-7, B-8, or B-9 wherein the linking group is oxaalkylene. Preferably, the linking group is $CH_2CH_2$—$O$—$CH_2CH_2CH_2$.

B-14. Compounds of formulae B, B-1, B-2, B-3, B-4, B-5, B-6, B-7, B-8, and B-9 may include compounds of formula B-14, which are compounds of formula B, B-1, B-2, B-3, B-4, B-5, B-6, B-7, B-8, or B-9 wherein the linking group is alkylene-[siloxanyl-alkylene]$_q$-, where q is from 1 to 50. An example of such a linking group is: —$(CH_2)_3$—$[Si(CH_3)_2$—$O$—$Si(CH_3)_2$—$(CH_2)_2]_q$—.

B-15. Compounds of formulae B, B-1, B-2, B-3, B-4, B-5, B-6, B-7, B-8, and B-9 may include compounds of formula B-15, which are compounds of formula B, B-1, B-2, B-3, B-4, B-5, B-6, B-7, B-8, or B-9 wherein the linking group is alkyleneoxy-carbamate-alkylene-cycloalkylene-carbamate-oxaalkylene, wherein cycloalkylene is optionally substituted with or 1, 2, or 3 independently selected alkyl groups (preferably $C_1$-$C_3$ alkyl, more preferably methyl). An example of such a linking group is —$[OCH_2CH_2]_q$—$OC(=O)$—$NH$—$CH_2$-$[1,3$-cyclohexylene$]$-$NHC(=O)O$—$CH_2CH_2$—$O$—$CH_2CH_2$—, wherein the cyclohexylene is substituted at the 1 and 5 positions with 3 methyl groups.

B-16. Compounds of formulae B, B-1, B-2, B-3, B-4, B-5, B-6, B-7, B-8, and B-9 may include compounds of formula B-16, which are compounds of formula B, B-1, B-2, B-3, B-4, B-5, B-6, B-7, B-8, or B-9 wherein Rg comprises styryl and the linking group is alkyleneoxy wherein each alkylene in alkyleneoxy is independently optionally substituted with hydroxyl. An example of such a linking group is —$O$—$(CH_2)_3$—. Another example of such a linking group is —$O$—$CH_2CH(OH)CH_2$—$O$—$(CH_2)_3$—.

B-17. Compounds of formulae B, B-1, B-2, B-3, B-4, B-5, B-6, B-7, B-8, and B-9 may include compounds of formula B-17, which are compounds of formula B, B-1, B-2, B-3, B-4, B-5, B-6, B-7, B-8, or B-9 wherein Rg comprises styryl and the linking group is alkyleneamine. An example of such a linking group is —NH—(CH$_2$)$_3$—.

B-18. Compounds of formulae B, B-1, B-2, B-3, B-4, B-5, B-6, B-7, B-8, and B-9 may include compounds of formula B-18, which are compounds of formula B, B-1, B-2, B-3, B-4, B-5, B-6, B-7, B-8, or B-9 wherein the linking group is oxaalkylene optionally substituted with hydroxyl, siloxy, or silyl-alkyleneoxy (where the alkyleneoxy is itself optionally substituted with hydroxyl). An example of such a linking group is —CH$_2$CH(G)CH$_2$—O—(CH$_2$)$_3$—, wherein G is hydroxyl. In another example, G is R$_3$SiO— wherein two R groups are trimethylsiloxy and the third is C$_1$-C$_8$ alkyl (preferably C$_1$-C$_3$ alkyl, more preferably methyl) or the third is C$_3$-C$_8$ cycloalkyl. In a further example, G is R$_3$Si—(CH$_2$)$_3$—O—CH$_2$CH(OH)CH$_2$—O—, wherein two R groups are trimethylsiloxy and the third is C$_1$-C$_8$ alkyl (preferably C$_1$-C$_3$ alkyl, more preferably methyl) or C$_3$-C$_8$ cycloalkyl. In a still further example, G is a polymerizable group, such as (meth)acrylate. Such compounds may function as cross-linkers.

B-19. Compounds of formulae B, B-1, B-2, B-3, B-4, B-5, B-6, B-7, B-8, and B-9 may include compounds of formula B-19, which are compounds of formula B, B-1, B-2, B-3, B-4, B-5, B-6, B-7, B-8, or B-9 wherein Rg comprises styryl and the linking group is amine-oxaalkylene optionally substituted with hydroxyl. An example of such a linking group is —NH—CH$_2$CH(OH)CH$_2$—O—(CH$_2$)$_3$—.

B-20. Compounds of formulae B, B-1, B-2, B-3, B-4, B-5, B-6, B-7, B-8, and B-9 may include compounds of formula B-20, which are compounds of formula B, B-1, B-2, B-3, B-4, B-5, B-6, B-7, B-8, or B-9 wherein Rg comprises styryl and the linking group is alkyleneoxy-carbamate-oxaalkylene. An example of such a linking group is —O—(CH$_2$)$_2$—N(H)C(=O)O—(CH$_2$)$_2$—O—(CH$_2$)$_3$—.

B-21. Compounds of formulae B, B-1, B-2, B-3, B-4, B-5, B-6, B-7, B-8, and B-9 may include compounds of formula B-21, which are compounds of formula B, B-1, B-2, B-3, B-4, B-5, B-6, B-7, B-8, or B-9 wherein the linking group is alkylene-carbamate-oxaalkylene. An example of such a linking group is —(CH$_2$)$_2$—N(H)C(=O)O—(CH$_2$)$_2$—O—(CH$_2$)$_3$—.

Formula C. Silicone-containing components of formulae A, B, B-1, B-2, B-3, B-4, B-5, B-6, B-7, B-8, B-9, B-10, B-11, B-12, B-13, B-14, B-15, B-18, and B-21 may include compounds of formula C, which are compounds of formula A, B, B-1, B-2, B-3, B-4, B-5, B-6, B-7, B-8, B-9, B-10, B-11, B-12, B-13, B-14, B-15, B-18, or B-21 having the structure:

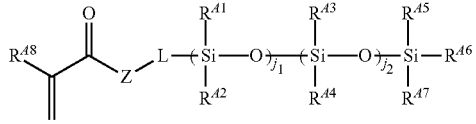

Formula C wherein
R$^{48}$ is hydrogen or methyl;
Z is O, S, or N(R$^{49}$); and
L, j1, j2, R$^{41}$, R$^{42}$, R$^{43}$, R$^{44}$, R$^{45}$, R$^{46}$, R$^{47}$, and R$^{49}$ are as defined in formula B or its various sub-formulae (e.g., B-1, B-2, etc.).

C-1. Compounds of formula C may include (meth)acrylates of formula C-1, which are compounds of formula C wherein Z is O.

C-2. Compounds of formula C may include (meth)acrylamides of formula C-2, which are compounds of formula C wherein Z is N(R$^{49}$), and R$^{49}$ is H.

C-3. Compounds of formulae C may include (meth)acrylamides of formula C-3, which are compounds of formula C wherein Z is N(R$^{49}$), and R$^{49}$ is C$_1$-C$_8$ alkyl that is unsubstituted or is optionally substituted as indicated above. Examples of R$^{49}$ include CH$_3$, —CH$_2$CH(OH)CH$_2$(OH), —(CH$_2$)$_3$-siloxanyl, —(CH$_2$)$_3$—SiR$_3$, and —CH$_2$CH(OH)CH$_2$—O—(CH$_2$)$_3$—SiR$_3$ where each R in the foregoing groups is independently selected from trimethylsiloxy, C$_1$-C$_8$ alkyl (preferably C$_1$-C$_3$ alkyl, more preferably methyl), and C$_3$-C$_8$ cycloalkyl. Further examples of R$^{49}$ include: —(CH$_2$)$_3$—Si(Me)(SiMe$_3$)$_2$, and —(CH$_2$)$_3$—Si(Me$_2$)-[O—SiMe$_2$]$_{1-10}$—CH$_3$.

Formula D. Compounds of formula C may include compounds of formula D:

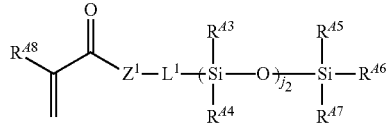

Formula D wherein
R$^{48}$ is hydrogen or methyl;
Z$^1$ is O or N(R$^{49}$);
L$^1$ is alkylene containing 1 to 8 carbon atoms, or oxaalkylene containing 3 to 10 carbon atoms, wherein L$^1$ is optionally substituted with hydroxyl; and
j2, R$^{43}$, R$^{44}$, R$^{45}$, R$^{46}$, R$^{47}$, and R$^{49}$ are as defined above in formula B or its various sub-formulae (e.g., B-1, B-2, etc.).

D-1. Compounds of formula D may include compounds of formula D-1, which are compounds of formula D wherein L$^1$ is C$_2$-C$_5$ alkylene optionally substituted with hydroxyl. Preferably L$^1$ is n-propylene optionally substituted with hydroxyl.

D-2. Compounds of formula D may include compounds of formula D-2, which are compounds of formula D wherein L$^1$ is oxaalkylene containing 4 to 8 carbon atoms optionally substituted with hydroxyl. Preferably L$^1$ is oxaalkylene containing five or six carbon atoms optionally substituted with hydroxyl. Examples include —(CH$_2$)$_2$—O—(CH$_2$)$_3$—, and —CH$_2$CH(OH)CH$_2$—O—(CH$_2$)$_3$—.

D-3. Compounds of formulae D, D-1, and D-2 may include compounds of formula D-3, which are compounds of formula D, D-1, or D-2 wherein Z$^1$ is O.

D-4. Compounds of formulae D, D-1, and D-2 may include compounds of formula D-4, which are compounds of formula D, D-1, or D-2 wherein Z$^1$ is N(R$^{49}$), and R$^{49}$ is H.

D-5. Compounds of formulae D, D-1, and D-2 may include compounds of formula D-5, which are compounds of formula D, D-1, or D-2 wherein Z$^1$ is N(R$^{49}$), and R$^{49}$ is C$_1$-C$_4$ alkyl optionally substituted with 1 or 2 substituents selected from hydroxyl, siloxy, and C$_1$-C$_6$ alkyl-siloxanyl-.

D-6. Compounds of formulae D, D-1, D-2, D-3, D-4, and D-5 may include compounds of formula D-6, which are compounds of formula D, D-1, D-2, D-3, D-4, or D-5 wherein j2 is 1.

D-7. Compounds of formulae D, D-1, D-2, D-3, D-4, and D-5 may include compounds of formula D-7, which are compounds of formula D, D-1, D-2, D-3, D-4, or D-5 wherein j2 is from 2 to 220, or from 2 to 100, or from 10 to 100, or from 24 to 100, or from 4 to 20, or from 4 to 10.

D-8. Compounds of formulae D, D-1, D-2, D-3, D-4, D-5, D-6, and D-7 may include compounds of formula D-8, which are compounds of formula D, D-1, D-2, D-3, D-4, D-5, D-6, or D-7 wherein $R^{43}$, $R^{44}$, $R^{45}$, $R^{46}$, and $R^{47}$ are independently $C_1$-$C_6$ alkyl or siloxy. Preferably $R^{43}$, $R^{44}$, $R^{45}$, $R^{46}$, and $R^{47}$ are independently selected from methyl, ethyl, n-propyl, n-butyl, and trimethylsiloxy. More preferably, $R^{43}$, $R^{44}$, $R^{45}$, $R^{46}$, and $R^{47}$ are independently selected from methyl, n-butyl, and trimethylsiloxy.

D-9. Compounds of formulae D, D-1, D-2, D-3, D-4, D-5, D-6, and D-7 may include compounds of formula D-9, which are compounds of formula D, D-1, D-2, D-3, D-4, D-5, D-6, or D-7 wherein $R^{43}$ and $R^{44}$ are independently $C_1$-$C_6$ alkyl (e.g., methyl or ethyl) or siloxy (e.g., trimethylsiloxy), and $R^{45}$, $R^{46}$, and $R^{47}$ are independently $C_1$-$C_6$ alkyl (e.g., methyl, ethyl, n-propyl, or n-butyl).

Formula E. The silicone-containing component may comprise a multi-functional silicone-containing component. Thus, for example, the silicone-containing component of formula A may comprise a bifunctional material of formula E:

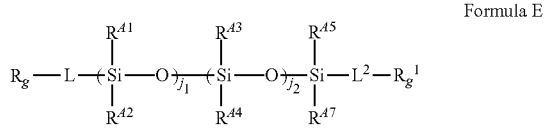

Formula E wherein $R_g$, L, j1, j2, $R^{A1}$, $R^{A2}$, $R^{A3}$, $R^{A4}$, $R^{A5}$, and $R^{A7}$ are as defined above for formula B or its various sub-formulae (e.g., B-1, B-2, etc.);

$L^2$ is a linking group; and $R_g^1$ is a polymerizable group.

E-1. Compounds of formula E may include compounds of formula E-1, which are compounds of formula E wherein Rg and $Rg^1$ are each a vinyl carbonate of structure $CH_2$=CH—O—C(=O)—O— or structure $CH_2$=C($CH_3$)—O—C(=O)—O—.

E-2. Compounds of formula E may include compounds of formula E-2, which are compounds of formula E wherein Rg and $Rg^1$ are each (meth)acrylate.

E-3. Compounds of formula E may include compounds of formula E-3, which are compounds of formula E wherein Rg and $Rg^1$ are each (meth)acrylamide, wherein the nitrogen group may be substituted with $R^{49}$ (wherein $R^{49}$ is as defined above).

E-4. Suitable compounds of formulae E, E-1, E-2, and E-3 include compounds of formula E-4, which are compounds of formula E, E-1, E-2, or E-3 wherein j1 is zero and j2 is from 1 to 220, or j2 is from 1 to 100, or j2 is from 1 to 50, or j2 is from 1 to 20.

E-5. Suitable compounds of formulae E, E-1, E-2, and E-3 include compounds of formula E-5, which are compounds of formula E, E-1, E-2, or E-3, wherein j1 and j2 are independently from 4 to 100.

E-6. Suitable compounds of formulae E, E-1, E-2, E-3, E-4, and E-5 include compounds of formula E-6, which are compounds of formula E, E-1, E-2, E-3, E-4, or E-5 wherein $R^{A1}$, $R^{A2}$, $R^{A3}$, $R^{A4}$, and $R^{A5}$ are independently at each occurrence $C_1$-$C_6$ alkyl, preferably they are independently $C_1$-$C_3$ alkyl, or preferably, each is methyl.

E-7. Suitable compounds of formulae E, E-1, E-2, E-3, E-4, E-5, and E-6 include compounds of formula E-7, which are compounds of formula E, E-1, E-2, E-3, E-4, E-5, or E-6 wherein $R^{A7}$ is alkoxy-alkyleneoxy-alkyl, preferably it is a methoxy capped polyethyleneoxyalkyl of formula $CH_3O$—$[CH_2CH_2O]_p$—$CH_2CH_2CH_2$, wherein p is a whole number from 1 to 50, or from 1 to 30, or from 1 to 10, or from 6 to 10.

E-8. Suitable compounds of formulae E, E-1, E-2, E-3, E-4, E-5, E-6, and E-7 include compounds of formula E-8, which are compounds of formula E, E-1, E-2, E-3, E-4, E-5, E-6, or E-7 wherein L comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

E-9. Suitable compounds of formulae E, E-1, E-2, E-3, E-4, E-5, E-6, E-7, and E-8 include compounds of formula E-9, which are compounds of formula E, E-1, E-2, E-3, E-4, E-5, E-6, E-7, or E-8 wherein $L^2$ comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

Examples of silicone-containing components suitable for use in the invention include, but are not limited to, compounds listed in the table below. Where the compounds in the table below include polysiloxane groups, the number of Si repeat units in such compounds, unless otherwise indicated, is preferably from 3 to 100, more preferably from 3 to 40, or still more preferably from 3 to 20.

---

1 mono-methacryloxypropyl terminated mono-n-butyl terminated polydimethylsiloxanes (mPDMS) (preferably containing from 3 to 15 SiO repeating units)
2 mono-acryloxypropyl terminated mono-n-butyl terminated polydimethylsiloxane
3 mono(meth)acryloxypropyl terminated mono-n-methyl terminated polydimethylsiloxane
4 mono(meth)acryloxypropyl terminated mono-n-butyl terminated polydiethylsiloxane
5 mono(meth)acryloxypropyl terminated mono-n-methyl terminated polydiethylsiloxane
6 mono(meth)acrylamidoalkylpolydialkylsiloxanes
7 mono(meth)acryloxyalkyl terminated mono-alkyl polydiarylsiloxanes
8 3-methacryloxypropyltris(trimethylsiloxy)silane (TRIS)
9 3-methacryloxypropylbis(trimethylsiloxy)methylsilane
10 3-methacryloxypropylpentamethyl disiloxane
11 mono(meth)acrylamidoalkylpolydialkylsiloxanes
12 mono(meth)acrylamidoalkyl polydimethylsiloxanes
13 N-(2,3-dihydroxypropane)-N'-(propyl tetra(dimethylsiloxy) dimethylbutylsilane)acrylamide
14 N-[3-tris(trimethylsiloxy)silyl]-propyl acrylamide (TRIS-Am)

-continued
| | |
|---|---|
| 15 | 2-hydroxy-3-[3-methyl-3,3-di(trimethylsiloxy)silylpropoxy]-propyl methacrylate (SiMAA) |
| 16 | 2-hydroxy-3-methacryloxypropyloxypropyl-tris(trimethylsiloxy)silane |
| 17 | mono-(2-hydroxy-3-methacryloxypropyl)-propyl ether terminated mono-n-butyl terminated polydimethylsiloxanes (OH-mPDMS) (containing from 4 to 30, or from 10 to 20, or from 4 to 8 SiO repeat units) |
18
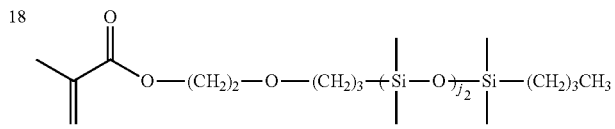
19
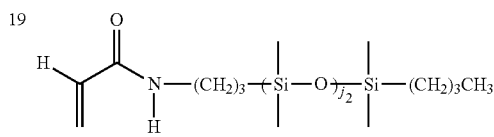
20
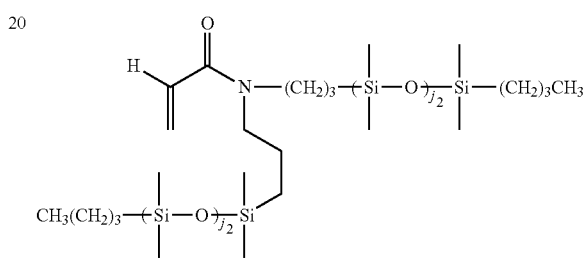
21
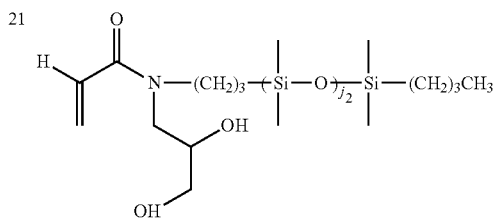
22
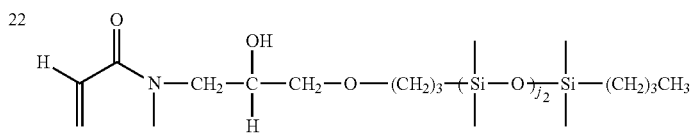
23
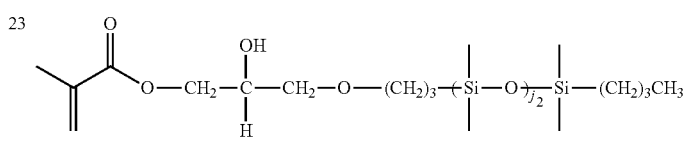
24
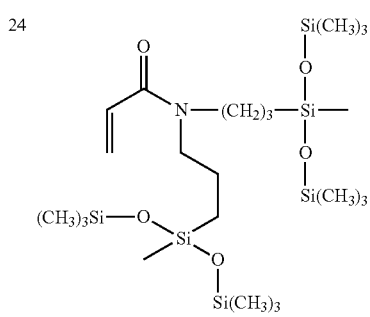

Additional non-limiting examples of suitable silicone-containing components are listed in the table below. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

25

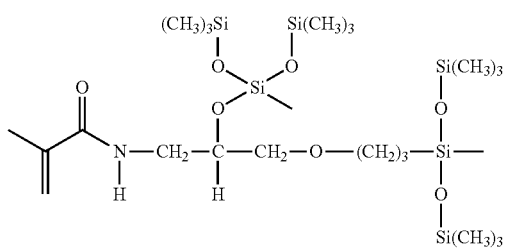

26

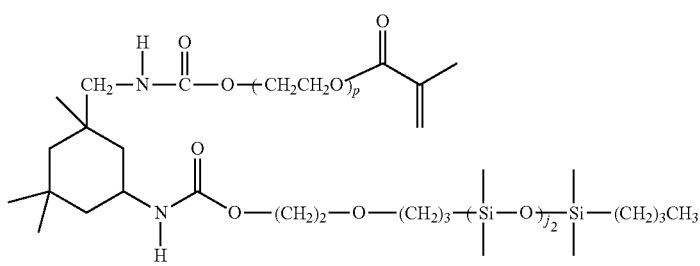

p is 1 to 10

27

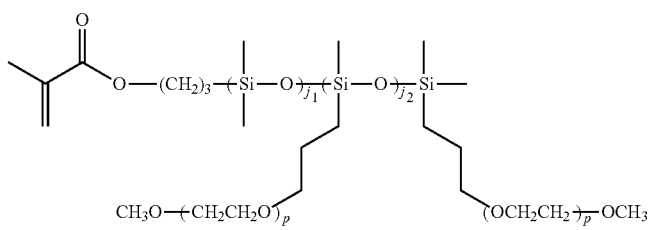

p is 5-10

28

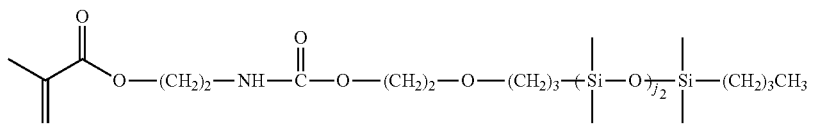

29

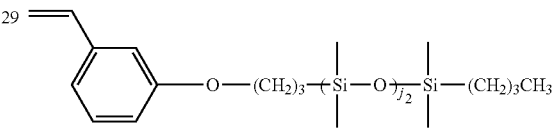

30  1,3-bis[4-(vinyloxycarbonyloxy)but-1-yl]tetramethyl-disiloxane
31  3-(vinyloxycarbonylthio) propyl-[tris(trimethylsiloxy)silane]
32  3-[tris(trimethylsiloxy)silyl] propyl allyl carbamate
33  3-[tris(trimethylsiloxy)silyl] propyl vinyl carbamate
34  tris(trimethylsiloxy)silylstyrene (Styryl-TRIS)

-continued

35 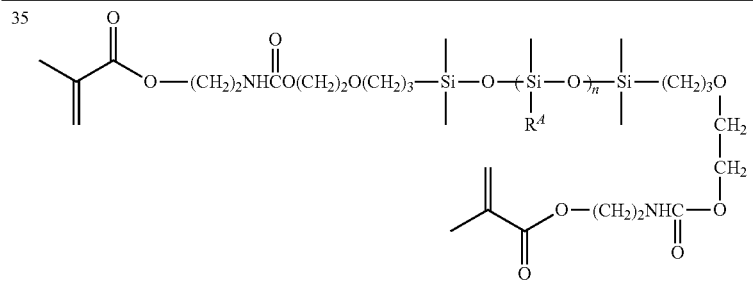

$R^A = CH_3$ (a) or $CH_2CH_2CF_3$ (b) or
$CH_2-(CH_2)_2-[OCH_2CH_2]_{1-10}-OCH_3$ (c); a + b + c = n

36 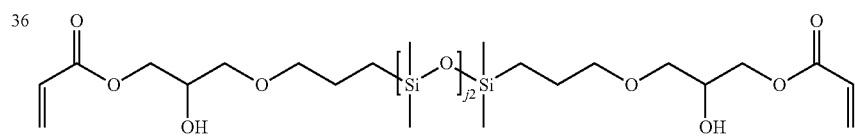

37 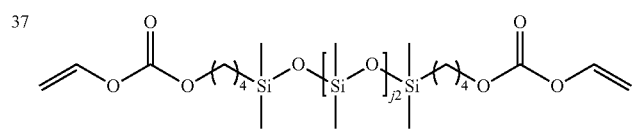

38 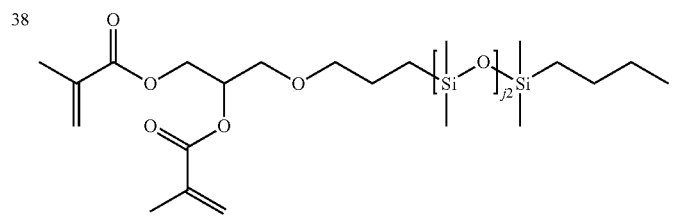

39 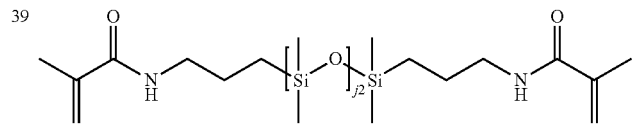

40 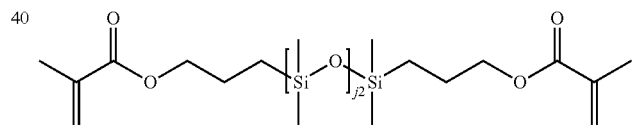

41 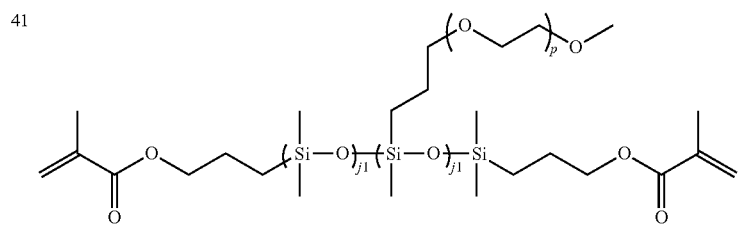

j1 = 80-90
j2 = 5-6
p = 7-8

Silicone-containing components may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive monomer mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

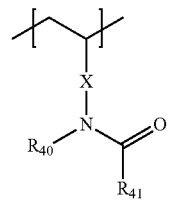

Formula G1

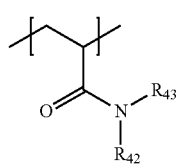

Formula G2 wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted C$_1$ to C$_2$ alkyl groups. X may be a direct bond, and R$_{40}$ and R$_{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N,N'-dimethylurea, N,N-dimethylacrylamide, methacrylamide, and acyclic amides of Formulae G2 and G3:

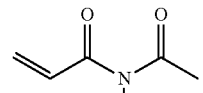

Formula G2

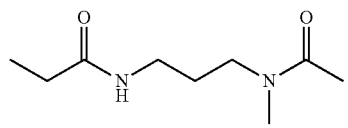

Formula G3

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

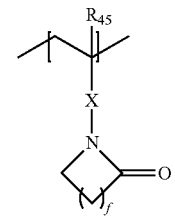

Formula G4 wherein R$_{45}$ is a hydrogen atom or methyl group; wherein f is a number from 1 to 10; wherein X is a direct bond, —(CO)—, or —(CONHR$_{46}$)—, wherein R$_{46}$ is a C$_1$ to C$_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

Cyclic polyamides may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth) acrylates. Any of the monomers listed as suitable hydrophilic monomers may be used as comonomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl)amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), 3-((3-(methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethylacetamide (PVMA), polydimethylacrylamide (PDMA), polyvinylacetamide (PNVA), poly hydroxyethyl (meth)acrylamide, polyacrylamide, and copolymers and mixtures thereof.

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides may be non-polymerizable, and in this case, are incorporated into the silicone hydrogels as semi-interpenetrating networks. The polyamides are entrapped or physically retained within the silicone hydrogels. Alternatively, the polyamides may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-linking Agents

It is generally desirable to add one or more cross-linking agents, also referred to as cross-linking monomers, multi-functional macromers, and prepolymers, to the reactive mixture. The cross-linking agents may be selected from bifunctional crosslinkers, trifunctional crosslinkers, tetra-functional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allyl methacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes α, ω-bismethacryloxypropyl polydimethylsiloxane.

Cross-linking agents that have rigid chemical structures and polymerizable groups that undergo free radical polymerization may also be used. Non-limiting examples of suitable rigid structures include cross-linking agents comprising phenyl and benzyl moieties, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described above, such as compounds of Formula E (and its sub-formulae) and the multi-functional compounds shown in the tables above.

Further Constituents

If desired, the reactive monomer mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, non-polymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445 the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms. Specific diluents which may be used include 1-ethoxy-2-propanol, diisopropyl aminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus an a-diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine eoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Diazo thermal initiators may also be used, such as azobisisobutyronitrile (AIBN), 2,2'-azobis(2-methylbutyronitrile) (AMBN) or similar compounds.

Commercially available visible light initiator systems include Irgacure® 819, Irgacure® 1700, Irgacure® 1800, Irgacure® 819, Irgacure® 1850 (all from Ciba Specialty Chemicals) and Lucrin® TPO initiator (available from BASF). Commercially available UV photoinitiators include Darocur® 1173 and Darocur® 2959 (Ciba Specialty Chemicals). These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the ophthalmic devices of the invention may comprise, in addition to a population of core-shell particles described herein, any of the polymerizable compounds and optional components described above.

Preferred reactive mixtures may comprise: a hydroxyphenyl phenanthroline of formula I and a hydrophilic monomer.

Preferred reactive mixtures may comprise: a population of core-shell particles described herein; and a hydrophilic monomer selected from DMA, NVP, HEMA, VMA, NVA, methacrylic acid, and mixtures thereof. Preferred are mixtures of HEMA and methacrylic acid.

Preferred reactive mixtures may comprise: a population of core-shell particles described herein, a hydrophilic monomer, and a silicone-containing component.

Preferred reactive mixtures may comprise: a population of core-shell particles described herein, a hydrophilic monomer, and a silicone-containing component comprising a compound of formula D (or its sub-formulae, such as D-1, D-2, etc.).

Preferred reactive mixtures may comprise: a population of core-shell particles described herein, a hydrophilic monomer selected from DMA, NVP, HEMA, VMA, NVA, and mixtures thereof, a silicone-containing component comprising a compound of formula D (or its sub-formulae, such as D-1, D-2, etc.); and an internal wetting agent.

Preferred reactive mixtures may comprise: a population of core-shell particles described herein, a hydrophilic monomer selected from DMA, HEMA and mixtures thereof; a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof, and a wetting agent (preferably PVP or PVMA). For the hydrophilic monomer, mixtures of DMA and HEMA are preferred. For the silicone containing component, mixtures of SiMAA and mPDMS are preferred.

The foregoing reactive mixtures may contain optional ingredients such as, but not limited to, one or more initiators, internal wetting agents, crosslinkers, other UV blockers, and diluents.

Curing of Hydrogels and Manufacture of Lenses

The reactive mixtures may be formed by any of the methods known in the art, such as shaking or stirring, and used to form polymeric articles or devices by known methods. The reactive components are mixed together either with or without a diluent to form the reactive mixture.

For example, hydrogels may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a silicone hydrogel contact lens may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble components such as inorganic salts or release agents, wetting agents, slip agents, pharmaceutical and nutraceutical compounds, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

Silicone hydrogel ophthalmic devices (e.g., contact lenses) described herein preferably have one or more of (and in some cases all of) the following properties. All values are prefaced by "about," and the devices may have any combination of the listed properties. The properties may be determined by methods known to those skilled in the art, for instance as described in United States pre-grant publication US20180037690, which is incorporated herein by reference.

[$H_2O$]%: at least 20%, or at least 25%

Haze: 30% or less, or 10% or less

Kruss DCA (°): 1000 or less, or 500 or less

Tensile Modulus (psi): 120 or less, or 80 to 120

Dk (barrers): at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less

Tablet Formation

In some embodiments, the system can include an indicator encapsulated within a tablet. The tablet can be optically transparent. The tablet can be formed from a porous polymer membrane formed from a thermoplastic polymer. The thermoplastic polymer can have a $T_g$ greater than 121° C. The porous polymer membrane can have a pore size larger than that of the capping agent but smaller than the average particle size of the population of nanoparticles. The pore size of the porous polymer membrane can be from 5 nm to 75 nm. For example, from 5 nm to 20 nm, from 5 nm to 30 nm, from 5 nm to 40 nm, from 5 nm to 50 nm, from 5 nm to 60 nm, or from 20 nm to 75 nm.

Other Applications and Methods of Use

The systems disclosed herein may also be useful in the pesticide, food, and/or medical industry. The systems and methods can be used to indicate the period of time elapsed since the occurrence of a triggering event. The methods can be used to visually indicate, for example, the time period elapsed since an article has been removed from its packaging, the period of time elapsed since an article or composition has been prepared, and/or the period of time that an article has been in use. In some embodiments, the indicator can function as a compliance indicator. For example, the indicator can indicate when a desired time period has elapsed since the article was removed from its packaging. For example, indicating when the article needs to be replaced. In some embodiments the system can be use in bandages, orthodontic devices, implantable medical devices, or ophthalmic device. For example, it can indicate when orthodontic devices such as retainers, expander, positioner, or spacers need to be replaced. It can also indicate when bandages need to be replaced.

The examples below are intended to further illustrate certain aspects of the materials and methods described herein, and is not intended to limit the scope of the claims

EXAMPLES

Example 1: Synthesis of Nanoparticle-Type Optical Indicators

Gold nanoparticles were synthesized via a seed-mediated method. First, seed precursor was synthesized using a single-pot nucleation process. A solution of gold (III) chloride hydrate (Sigma-Aldrich) and trisodium citrate dihydrate (Sigma-Aldrich) was prepared with final concentrations of $2.5 \times 10^{-4}$ and $10^{-4}$ M, respectively, in 20 ml of MilliQ water (18.2 MΩ.cm at 20° C., Millipore Sigma) within a glass scintillation vial (VWR). MilliQ water was used to prepared aqueous solutions throughout the rest of the examples, unless otherwise specified. Then, 60 µl of freshly prepared, ice-cold sodium borohydrate (0.1 M, Sigma-Aldrich) was added to the vial under vigorous stirring (2000 rpm), and the solution was left stirring for 1 min while the seed precursor nucleated. The seed precursor was left overnight in the dark in ambient conditions. Next, the seed precursor solution was syringe filtered (0.2 µm, VWR) and stored at 4° C. in the dark until use.

Gold nanoparticles were synthesized with differing sizes, shapes and capping agents. To grow nanoparticles that presented a red color and were capped with cetyltrimethylammonium bromide (CTAB), gold (III) chloride hydrate (0.64 ml, 11 mM) and silver nitrate (0.096 ml, 0.01 M, Sigma-Aldrich) were added to a 15 ml solution of CTAB (1.466 mM) in a 20 ml scintillation vial under moderate stirring (900 rpm); the solution was left to stir for 1 minute. Then, L-ascorbic acid (0.103 mL, 0.1 M) was added dropwise. Upon addition of the last drop, nanoseed precursor (0.6 ml) was added immediately and left to stir moderately for 1.5 minutes. This sample is denoted as Indicator 1 (I1). To grow red-colored nanoparticles capped with poly(vinylpyrrolidone) (PVP, Sigma-Aldrich), the process was repeated but silver nitrate and CTAB were excluded and instead the gold (III) chloride hydrate was added to a solution of PVP (200 mM). This sample is denoted as I2. To grow red-colored nanoparticles capped with sodium dodecyl sulfate (SDS, Sigma-Aldrich), PVP was replaced with sodium iodide (0.25 mM) and SDS (24 mM) during synthesis. This sample is denoted as I3. To grow red-colored nanoparticles capped with Pluronic F-127 (Sigma-Aldrich), PVP was replaced with Pluronic F-127 (40 mM) during synthesis. This sample is denoted as I4. To grow nanoparticles that presented a blue color, gold (III) chloride hydrate (0.64 ml, I1 mM) and silver nitrate (0.192 ml, 0.01 M, Sigma-Aldrich) were added to a 15 ml solution of CTAB (7.33 mM) in a 20 ml scintillation vial under moderate stirring (900 rpm.); the solution was left to stir for 1 minute. Then, L-ascorbic acid (0.103 mL, 0.1 M, Sigma-Aldrich) was added dropwise. Upon addition of the last drop, nanoseed precursor (240 µl) was added immediately and left to stir moderately for 5 minutes. This sample is denoted as I5. To grow blue-colored nanoparticles capped with Tween 80 (Sigma-Aldrich), the respective process was repeated but CTAB was replaced by Tween 80 (5 mM) during synthesis. This sample is denoted as I6. To grow blue-colored nanoparticles capped with SDS, the respective process was repeated but CTAB was replaced by SDS (24 mM) during synthesis. This sample is denoted as I7. Samples were centrifuged (15,000 rcf, 15 minutes) and resuspended in a desired concentration of capping agent, as specified.

Figure 1B:
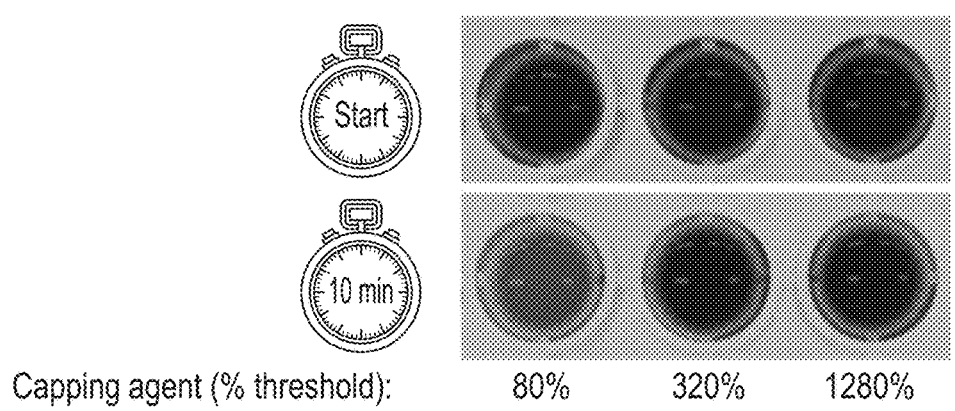
FIG. 1B depicts a demonstration of threshold-based color change based on capping agent concentration for a two-particle purple-to-red color transition (blue color-losing+red color-retaining) for manual mixing within microwell plate.
Figure 1C:
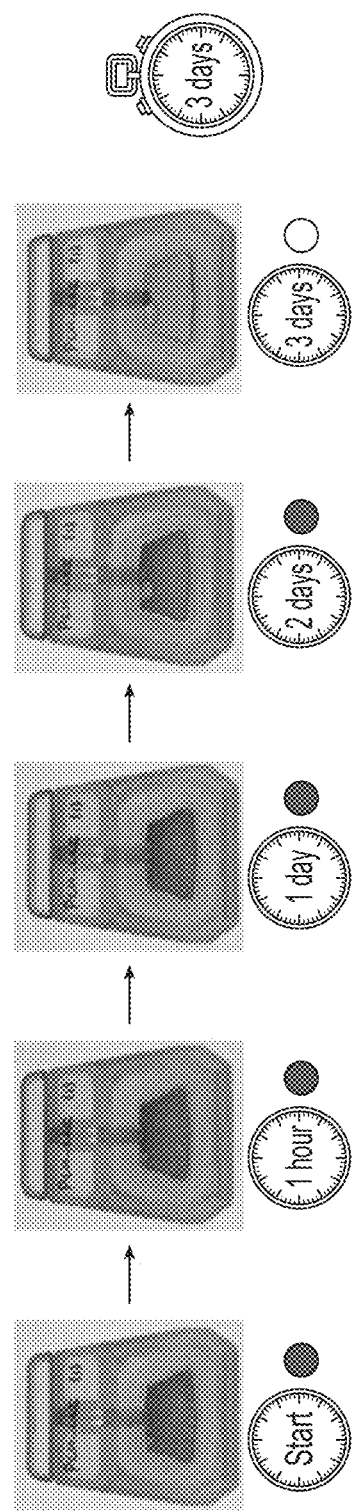
FIGS. 1C to 1E depict demonstrations of programmable color changes within dialysis cassettes for color-to-clear transitions. The single-particle system was programmed by concentration of capping agent to be activate at 3 days (FIG. 1C), 5 days (FIG. 1D) or 8 days (FIG. 1E).
Figure 1D:
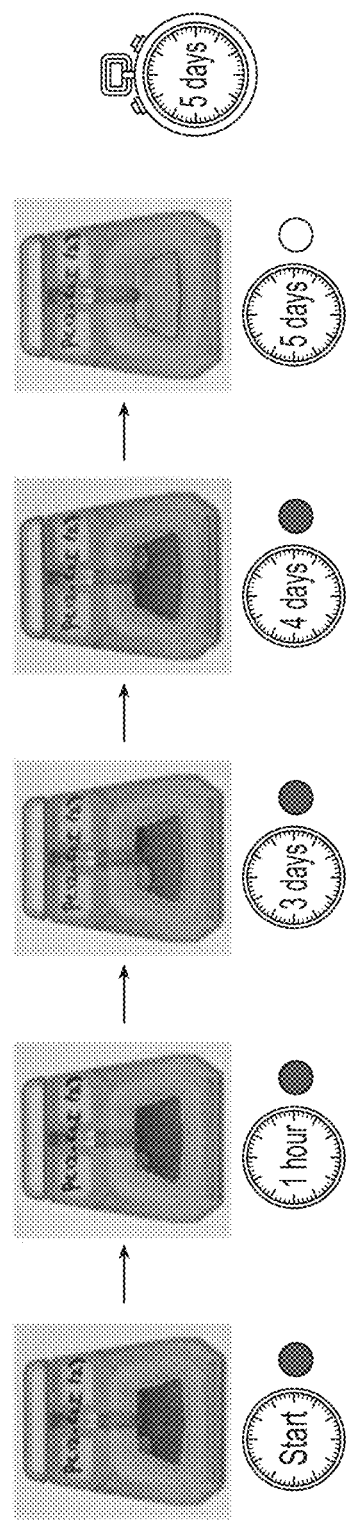
Figure 1E:
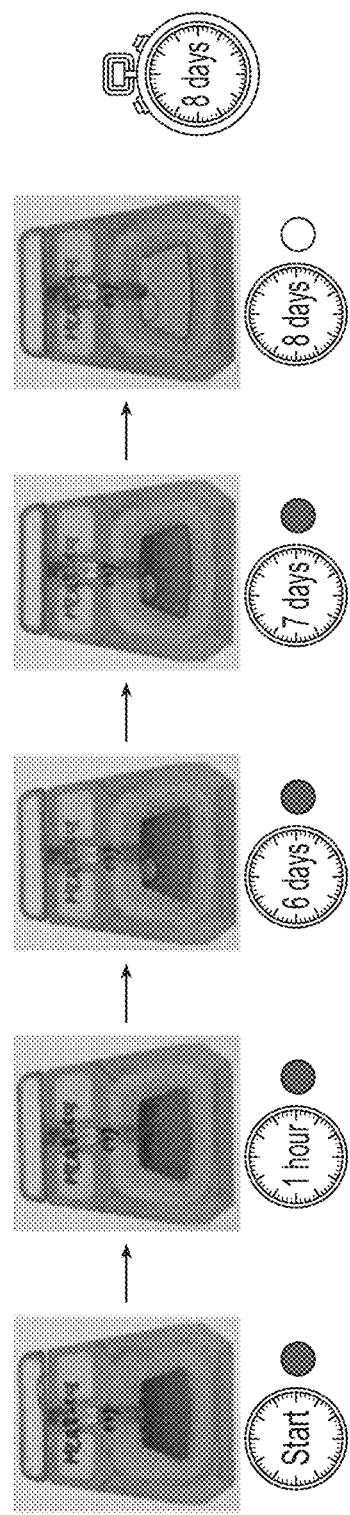

Example 2: Assessment of Discrete, Threshold-Based Color Transitions of Indicators in Stationary Microwell Plates To assess if color transitions for our indicators were indeed rapid and based on a discrete concentration threshold of capping agent, first, a 3× concentrated solution of simulated tear fluid (STF) was prepared by dissolving sodium chloride (20.34 g/l, Sigma-Aldrich), sodium bicarbonate (6.54 g/l, Sigma-Aldrich), calcium chloride (0.192 g/l, Sigma-Aldrich) and potassium chloride (4.14 g/l, Sigma-Aldrich) in MilliQ water. We centrifuged (15,000 rcf, 15 minutes, thrice) solutions of I5-a color-changing indicator, concentrated them 2× and resuspended them for varying concentrations of CTAB (1.6 mM, 6.4 mM or 25.6 mM). In addition, we centrifuged a solution of I4-a color-retaining indicator, concentrated the concentrated it 2× and resuspended it in MilliQ. For a color-to-color (purple-to-red color) transition, each concentrated solution of I4 was mixed with an aliquot of I5 and added 200 µl of those solutions to adjacent wells in a 96-well microplate (VWR) and imaged the microwell plate (FIG. 1B, top row). The critical micelle concentration (CMC) of CTAB is approximately 1 mM at room temperature, so final CTAB concentrations in the mixtures were chosen slightly below (0.8 mM), above (3.2 mM) and significantly above (12.8 mM) the CMC. Immediately after the initial image, 100 µl of 3× concentrated STF was added to each well, diluting the STF concentration to 1×. Upon addition of the STF, I5 (0.8 mM) began to instantaneously lose color, revealing a red color, with the color change saturating by 10 minutes (FIG. 1B, bottom row). The mixtures with I5 (3.2 mM) and I5 (12.8 mM) remained purple, demonstrating that no color loss occurred (FIG. 1B, bottom row). Taken together, the results showed that at a capping agent concentration near at the CMC, color-changing indicators will lose color rapidly, while those with higher concentrations of capping agent show no color change. In addition, the results showed that color-retaining indicators can be used in combination with color-changing indicators for discrete color-to-color transitions.

Example 3: Programming the Activation Time of Indicators in Receptacles

Figure 2A:
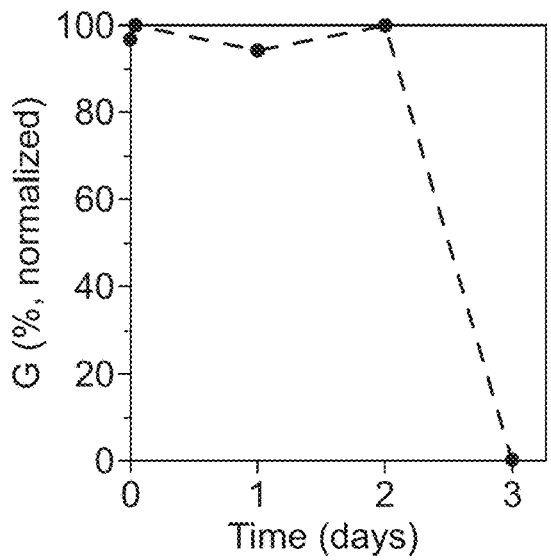
FIGS. 2A, 2B, and 2C depict analyses of colors for the samples shown in FIGS. 1C to 1E, and demonstrate that programmable color transitions are discrete and occurs rapidly near the target activation time. The G channel of the indicators' color was analyzed and normalized against the white background for color analysis.
Figure 2B:
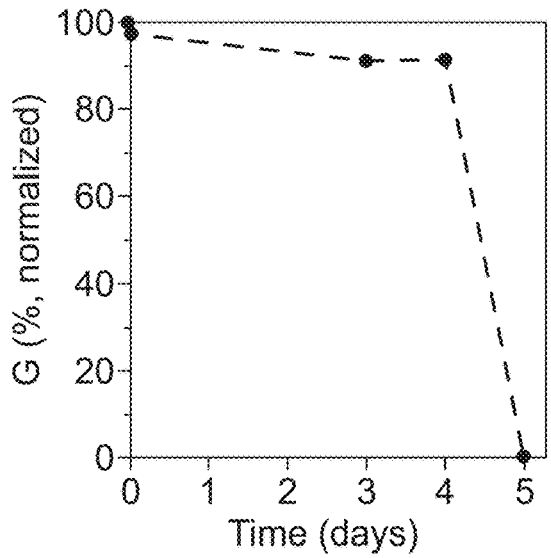
Figure 2C:
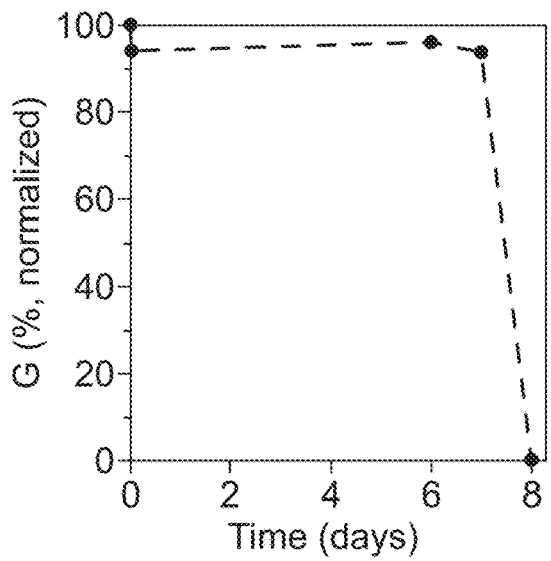
Figure 3:
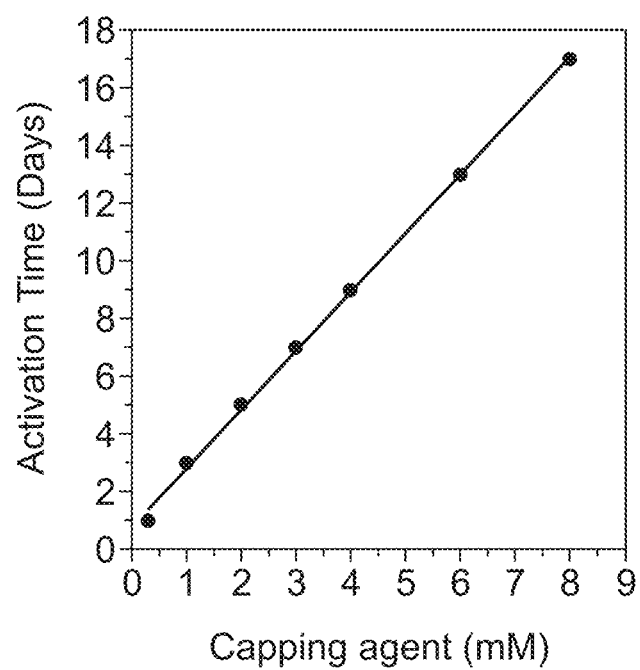
FIG. 3 shows that activation time of color indicators is programmable based on the initial concentration of capping agent in the receptacle. Data is shown for single-particle color-to-clear indicators.

To assess activation characteristics of the indicators in receptacles, we tested the indicators in dialysis cassettes (Thermo Fisher Scientific) with a molecular weight cutoff (MWCO) between the size of the indicator(s) and the molecular weight of the capping agent. Hence, capping agent can be released from the receptacle while indicators are retained. All tests were performed using dialysis cassettes with a MWCO of 3.5 kDa, at 37° C. (within an incubator, VWR) and in 1× STF, unless otherwise noted.
Programmable Color-to-Clear Transitions For color-to-clear transitions, solutions of I1 were centrifuged (15,000 rcf, 10 minutes, thrice), resuspended in varying concentrations of CTAB (once per round of centrifugation) and input into hydrated cassettes. The I1-containing receptacles were imaged (start image, time: 0 h) and placed in beakers containing enough STF (1×, 350 ml) to completely immerse the cassettes. The receptacles were then imaged (times: 0.5 h, 1 h, 1.5 h, 2 h, 2.5 h, 3 h, 3.5 h, 4 h, 5 h, 6 h, 7 h, 8 h, 24 h and then each 24 h interval after that)

to characterize the color progressions. The STF in the beakers was regularly replaced with fresh STF (1×, 350 ml). Indicators demonstrated color-to-clear transitions that were discrete, threshold responses (FIG. 1, C to E, and FIG. 2) and were programmable based on the concentration of capping agent initially within the cassettes (time: 0 h) (FIG. 3).

Programmable Color-to-Color-to-Clear Transitions

Figure 4A:
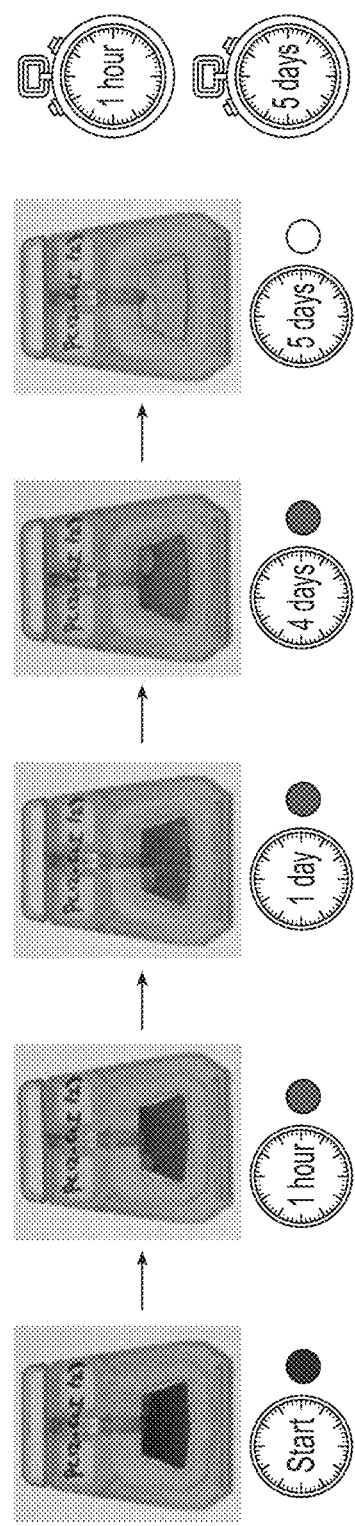
FIGS. 4A and 4B depict demonstrations of color-to-color-to-clear (purple-to-red-to-clear) color transitions based on two-particle systems (blue star-shaped particle+red spherical particle). The blue particle is less colloidally stable, prompting it to lose color earlier than the red particle (1 hour). Two different red particles were used for programmable color transitions at 1 hour and 5 days (FIG. 1A) and 1 hour and 9 days (FIG. 1), demonstrating that two color-change systems can be programmed to activate independently.
Figure 4B:
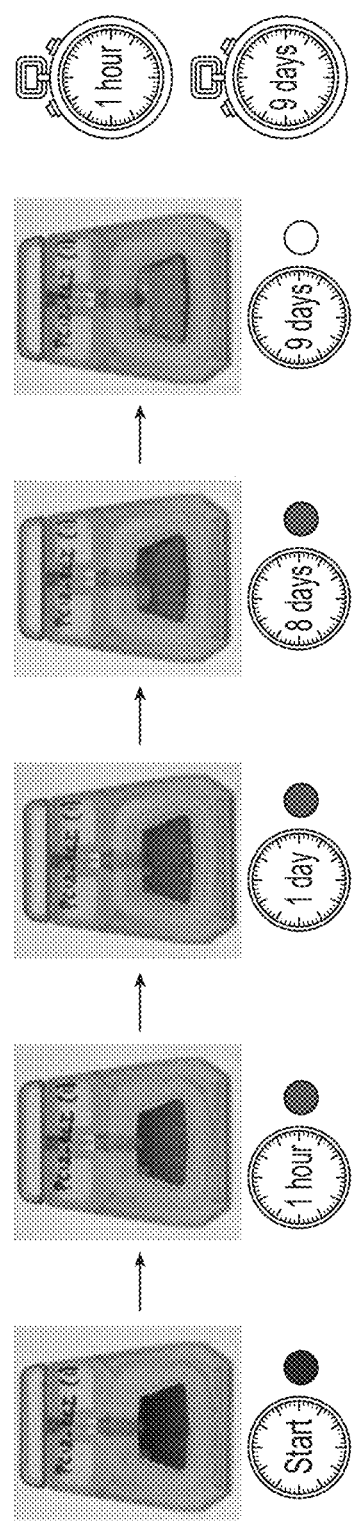

For color-to-color-to-clear transitions, solutions of I1 and I6 were centrifuged (15,000 rcf, 10 minutes, thrice), resuspended (once per round of centrifugation) in varying concentrations of CTAB and Tween 80, respectively, concentrated 2×, mixed and input into hydrated cassettes. The two-indicator-containing receptacles were imaged as previously described and placed within beakers containing STF. Indicators could be independently programmable, as shown in FIG. 4, in which the initial concentration of CTAB and Tween 80 were 2 mM and 0.015 mM (top row) or 4 mM and 0.015 mM (bottom row), and the samples showed that I6 activated at the 1 hour mark in both samples, as the capping agent concentrations were identical, and I1 activated at the 5-day (top row) or 9-day (bottom row) marks, based on different capping agent concentrations.

Delaying Activation of Indicators in the Receptacles

I1 and I7 were centrifuged (15,000 rcf, 10 minutes, thrice), resuspended in capping agent concentrations above their respective CMCs (1.5 mM and 10 mM, respectively, once per round of centrifugation) and input into hydrated cassettes. The indicator-containing receptacles were imaged (start image, time: 0 h), placed in beakers containing STF and an equimolar concentration of their respective capping agents and imaged as described above. As shown in FIG. 5, color transitions of indicators within the receptacles were demonstrated to be delayed indefinitely, as the net concentration of the capping agents remained consistent.

Color-Retaining Indicators

Color-to-color transitions can be made using a mixture of color-losing and color-retaining indicators. The capping agent(s) of color-retaining indicators do not diffuse out of the receptacle. The capping agent(s) can be kept within the receptacle by having the receptacle have a MWCO below the molecular weight of a color-retaining capping agent. In another embodiment, the capping agent can associate strongly to its indicator such that there is insignificant net diffusion of the capping agent out of the receptacle. To demonstrate that I2 and I4 are two examples of latter type of color-retaining indicator, solutions of I2 and I4 were centrifuged (15,000 rcf, 10 minutes, thrice), resuspended in MilliQ water (once per round of centrifugation) and input into hydrated cassettes. The indicator-containing receptacles were imaged (start image, time: 0 h), placed in beakers containing STF and imaged (times: 1 h, 2 h, 4 h, 8 h, 24 h, then each 24-h interval after that up to 1 week and then each 1-week interval). STF was regularly replaced with fresh STF (1×). Color-retaining indicators retained their color, as shown in FIG. 6.

Programmable Color-to-Color Transitions

For color-to-color-transitions, solutions of I4 and I7 were centrifuged (15,000 rcf, 10 minutes, thrice), resuspended (once per round of centrifugation) in MilliQ water and varying concentrations of SDS, respectively, concentrated 2×, mixed and input into hydrated cassettes. These receptacles were imaged (start time), placed into beakers containing STF (1×) and imaged as previously described. FIG. 7 shows a purple-to-red color transition that occurred with an initial SDS concentration of 8.5 mM within the receptacle.

Figure 8A:
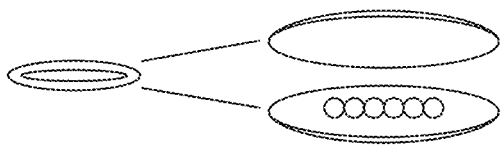
FIGS. 8A to 8G demonstrate integration of indicator into biomaterial and stability against autoclaving and various liquids. More specifically.
Figure 8B:
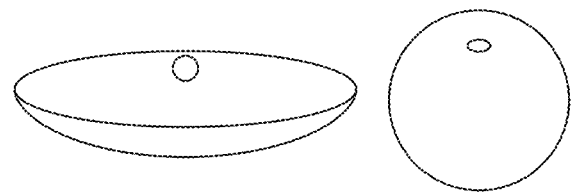

Example 4: Integration of Indicators into Contact Lenses and Stability Testing Against Sterilization Conditions and Consumer Liquids To input the indicators into a receptacle that can then be integrated into a biomedical device, solutions of I3 and I6 were centrifuged (15,000 rcf, 10 minutes, thrice), resuspended (once per round of centrifugation) in MilliQ water and equimolar concentrations of Tween 80, respectively, concentrated 10×, mixed with poly(ethylene glycol) (PEG, final concentration: 50 mM, 6 kDa or 20 kDa, Sigma-Aldrich) and allowed to dry under reduced pressure. A flake of dried indicator was placed onto a track-etched polycarbonate membrane (pore size: 15 nm, Sigma-Aldrich). Next, a second polycarbonate membrane was placed on top, sandwiching the indicators; a piece of filter paper was placed on top of the second polycarbonate membrane. A flat, solid stainless-steel sealer was heated by a heat gun (Wagner Spray Tech, set to approximately 500° C. with the sealer at a distance of ~1 cm away from the heating surface, 6 min) and pressed against the filter paper (1 minutes). After that, the filter paper was removed, and a hollow stainless-steel cutter with sharpened ends was heated as described above and pressed against the sealed membranes (1 minutes). This process formed a receptacle containing the indicators (FIG. 8A). I3 and I6 were resuspended within their receptacles in solutions of MilliQ water and Tween 80, respectively. Within a glove box, three drops of Etafilcon A monomer mix were placed within the posterior contact lens mold, the I3- or I6-containing receptacles were placed in the monomer mix, three additional drops of monomer mix were added, embedding the receptacle within the solution, and the solution was cured under UV light (20 minutes). Contact lenses were placed in a water bath (60° C.) and removed from the molds. Contact lenses containing I3- and I6-receptacles were then placed in contact lens packing solution and contact lens packing solution with equimolar Tween 80. FIGS. 8, B and D, each show a contact lense with a receptable containing I6 or I3, respectively, embedded within it.

Figure 8C:
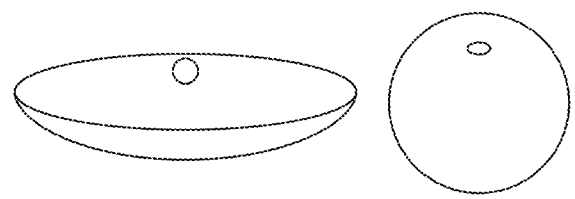
Figure 8D:
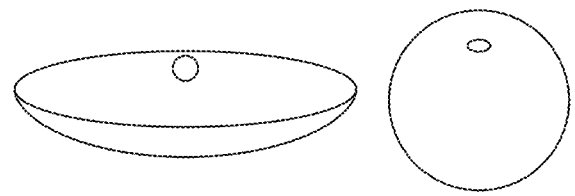
Figure 8E:
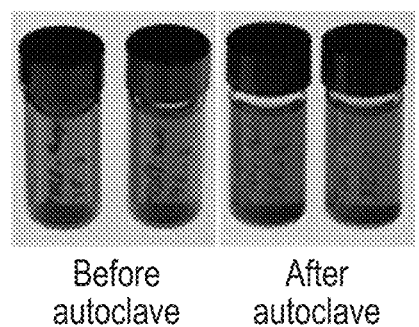
Figure 8F:
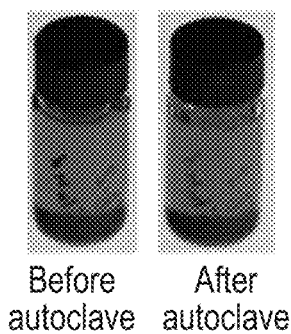

To form indicators in ring structure, a 2-μl drop of PEG was added onto a polycarbonate membrane and allowed to dry. Then, a 2-μl drop of a prepared solution of I3 was added onto the dried PEG. Indicator solutions dried in a ring structure. The sandwiching polycarbonate membranes were put into contact and sealed during the sealing process to maintain the ring structure after the indicators were resuspended. The rest of the process for sealing, cutting, resuspending and embedding the indicator-containing receptacle as well as forming the indicator-containing contact lens was repeated from above. FIG. 8C shows a contact lens with a receptable containing I3 in a ring structure embedded within the lens.

Figure 8G:
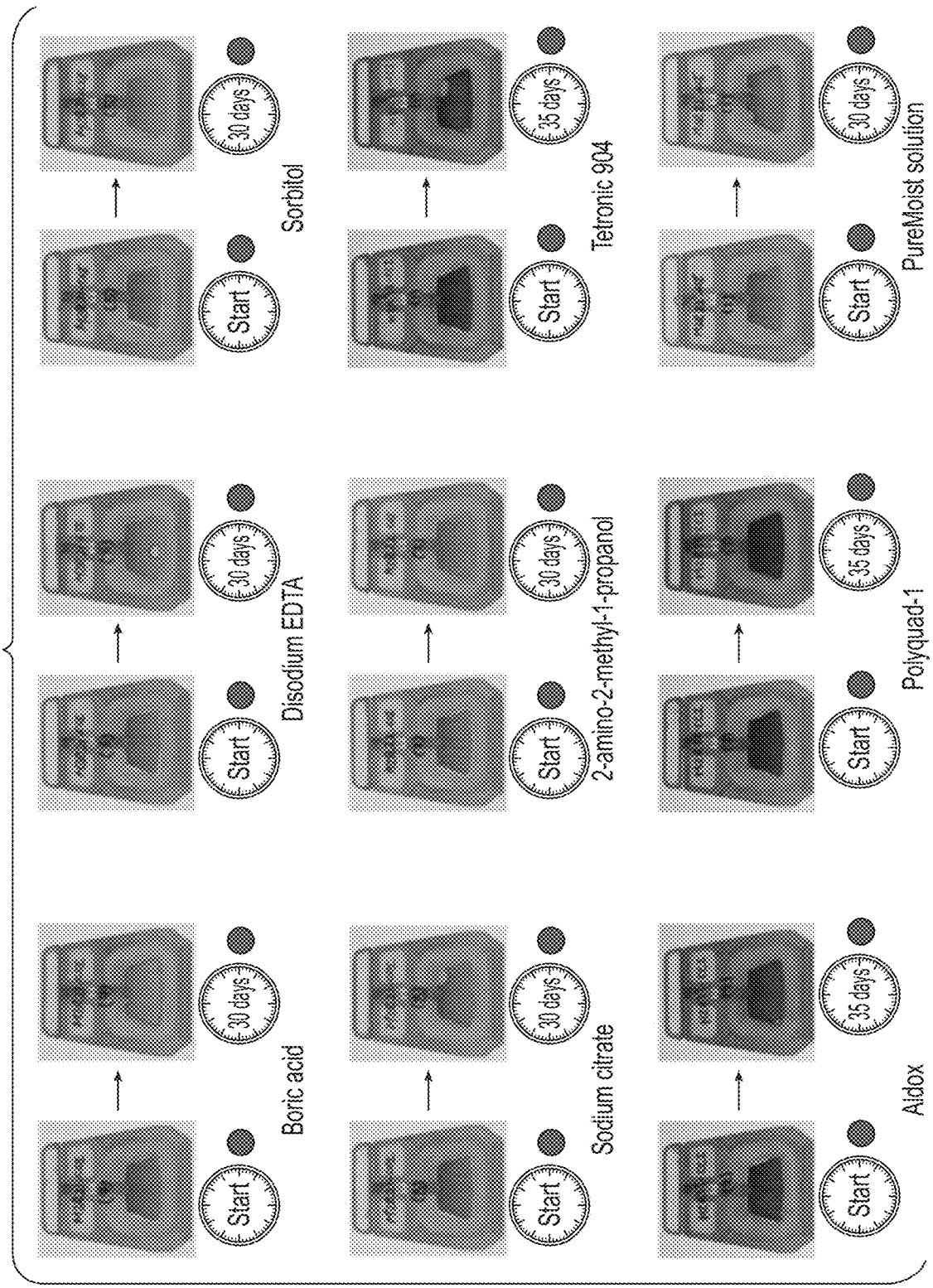

Indicators were tested for stability against autoclaving and various reagents. Prepared solutions of I3 (FIG. 8E) and a mixture of I4 and I7 (FIG. 8F) were autoclaved and remained colloidally stable afterwards. Prepared solutions of I1 were input in dialysis cassettes. The receptacles were then placed in solutions of and showed stability against boric acid (0.5%, Sigma-Aldrich), disodium ethylenediaminetetraacetic acid (EDTA, 0.07%, Sigma-Aldrich), sorbitol (1.0%, Sigma-Aldrich), sodium citrate (0.65%, Sigma-Aldrich), 2-amino-2-methyl-1-proponal (0.001%, Sigma-Aldrich), Tetronic 904 (0.05%, Sigma-Aldrich), Aldox (0.0005%, Sigma-Aldrich), polyquaternium-1 (0.0005%, Toronto Research Chemicals), (0.2%, Sigma-Aldrich) and PureMoist lens cleaning solution (FIG. 8G).

The systems, methods, compositions, and devices of the appended claims are not limited in scope by the specific materials and devices described herein, which are intended as illustrations of a few aspects of the claims. Any systems, methods, compositions, and devices that are functionally equivalent are intended to fall within the scope of the claims. Various modifications of the systems, methods, compositions, and devices in addition to those shown and described herein are intended to fall within the scope of the appended claims. Further, while only certain representative systems, methods, compositions, and devices disclosed herein are specifically described, other combinations of the systems, methods, compositions, and devices are also are intended to fall within the scope of the appended claims, even if not specifically recited. Thus, a combination of elements, components, or constituents may be explicitly mentioned herein or less, however, other combinations of elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

We claim:

1. A system for visually indicating the time elapsed since an article has been removed from a package, the system comprising:
   an indicator disposed on or within the article, wherein the article is enclosed within a sealable receptacle of the package; and
   a trigger disposed within the receptacle and in contact with the indicator;
   wherein the indicator is responsive to a change in a concentration of the trigger in contact with the indicator,
   wherein the indicator comprises a population of nanoparticles stabilized by a capping agent, and wherein the trigger comprises a solution comprising the capping agent in contact with the indicator,
   wherein when the article is removed from the receptacle and placed in contact with a solution containing a lower concentration of the trigger, the capping agent disassociates from the nanoparticles, thereby inducing aggregation of the population of nanoparticles; and
   wherein aggregation of the population of nanoparticles results in a color change.

2. The system of claim 1, wherein the trigger is present at a static concentration within the receptacle.

3. The system of claim 1, wherein the population of nanoparticles has an average particle size of from 5 nm to 100 nm as measured by transmission electron microscopy (TEM).

4. The system of claim 1, wherein the population of nanoparticles has a monodisperse particle size distribution.

5. The system of claim 1, wherein the nanoparticles have a spherical, a rod, a cone, a cylindrical, a shell, or a star shape.

6. The system of claim 1, wherein the nanoparticles have a homogenous particle shape.

7. The system of claim 1, wherein the nanoparticles comprise a mixture of particle shapes.

8. The system of claim 1, wherein the capping agent is non-covalently associated with the nanoparticles.

9. The system of claim 1, wherein the capping agent is biocompatible.

10. The system of claim 1, wherein the article comprises a medical device.

11. The system of claim 1, wherein the article comprises an ophthalmic device.

12. The system of claim 1, wherein the indicator is patterned on the article.

13. The system of claim 1, wherein the indicator is stable to autoclaving.

14. The system of claim 1, wherein removal of the article from the receptacle induces a change in concentration of the trigger in contact with the indicator.

15. The system of claim 14, wherein the change in the concentration of the trigger induces a change in a color of the indicator.

16. The system of claim 15, wherein the change in color comprises a change from a first color in the visible spectrum to a second color in the visible spectrum.

17. The system of claim 15, wherein the change in color comprises a change from a first color outside of the visible spectrum to a second color in the visible spectrum.

18. The system of claim 15, wherein the change in color comprises a change from a first color in the visible spectrum to a second color outside of the visible spectrum.

19. The system of claim 1, wherein the population of nanoparticles comprises a population of plasmonic nanoparticles.

20. The system of claim 19, wherein the population of plasmonic nanoparticles comprise gold, silver, platinum, or a combination thereof.

21. The system of claim 1, wherein the nanoparticles have a polyhedral shape.

22. The system of claim 21, wherein the nanoparticles have a cubic shape, an octahedral shape, a decahedral shape, a cuboctahedral shape, a tetrahedral shape, a rhombic dodecahedral shape, a truncated ditetragonal prismatic shape, or a truncated bitetrahedral shape.

23. The system of claim 1, wherein the capping agent comprises a surfactant.

24. The system of claim 23, wherein the surfactant comprises an anionic surfactant, a cationic surfactant, a non-ionic surfactant, an amphoteric surfactant, or a combination thereof.

25. The system of claim 23, wherein the surfactant comprises a phosphatide, a polyoxyethylene sorbitan fatty acid ester, a polyoxyethylene alkyl ether, stearic acid, benzalkonium chloride, calcium stearate, glycerol monostearate, cetostearyl alcohol, 3-[N,N-Dimethyl(3-palmitoylaminopropyl)ammonio]-propanesulfonate, N-Dodecyl-N,N-(dimethylammonio)butyrate, sodium dodecyl sulfate (SDS), sodium lauryl sulfate, octadecanoic acid, a poloxamer, a poloxamine, an alkyl aryl polyether sulfonate, palmitic acid, dodecylphosphonic acid, sodium oleate, sodium octanoate, cetyltrimethylammonium bromide, tetrabutylammonium hydroxide titrant, sodium dodecyl phosphonate, tetrabutylammonium palmitate, tetrabutylammonium laurate, a polysorbate, or a combination thereof.

26. The system of claim 1, wherein the capping agent comprises a polymer.

27. The system of claim 26, wherein the polymer comprises polyvinylpyrrolidone, polyvinyl alcohol, a polyalkylene oxide, a cellulosic polymer, tyloxapol, or a combination thereof.

28. The system of claim 1, wherein the capping agent disassociates from the nanoparticles at a rate selected such that the color change indicates a predetermined period of time has elapsed since the article has been removed from the receptacle.

29. The system of claim 28, wherein the predetermined period of time is from 30 minutes to 30 days.

30. The system of claim 1, wherein the indicator comprises a first population of nanoparticles stabilized by a first capping agent and a second population of nanoparticles stabilized by a second capping agent, and wherein the trigger comprises a solution comprising the first capping agent and the second capping in contact with the indicator.

31. The system of claim 30, wherein when the article is removed from the receptacle and placed in contact with a solution containing a lower concentration of the trigger, the first capping agent disassociates from first population of nanoparticles at a faster rate than the second capping agent disassociates from the second population of nanoparticles.

32. The system of claim 30, wherein when the article is removed from the receptacle and placed in contact with a solution containing a lower concentration of the trigger, the first capping agent disassociates from the first population nanoparticles, thereby inducing aggregation of the first population of nanoparticles and generating a first color change, then the second capping agent disassociates from the second population nanoparticles, thereby inducing aggregation of the second population of nanoparticles and generating a second color change.

33. The system of claim 30, wherein the first capping agent disassociates from the first population of nanoparticles at a first rate selected such that the first color change indicates a first predetermined period of time has elapsed since the article has been removed from the receptacle, and wherein the second capping agent disassociates from the second population nanoparticles at a second rate selected such that the second color change indicates a second predetermined period of time has elapsed since the article has been removed from the receptacle.

34. The system of claim 33, wherein the first predetermined period of time is from 10 minutes to two weeks and wherein the second predetermined period of time is from 30 minutes to 30 days, such as from 1 hour to 30 days.

35. The system of claim 1, wherein the article comprises a contact lens.

36. The system of claim 35, wherein the contact lens comprises a soft contact lens.

37. The system of claim 35, wherein the contact lens comprises a polyurethane, a thiourethane, a poly(meth)acrylate, a silicone hydrogel, or a combination thereof.

38. The system of claim 35, wherein the contact lens comprises a polymer derived from polymerization of a hydrophilic monomer, a silicone-containing component, or combinations thereof.

39. The system of claim 1, wherein the indicator is encapsulated within a tablet.

40. The system of claim 39, wherein the tablet is optically transparent.

41. The system of claim 39, wherein the tablet is formed from a porous polymer membrane.

42. The system of claim 41, wherein the porous polymer membrane is formed from a thermoplastic polymer having $T_g$ greater than 121° C.

43. The system of claim 41, wherein the porous polymer membrane has a pore size of from 5 nm to 75 nm.

44. The system of claim 41, wherein the indicator comprises a population of nanoparticles stabilized by a capping agent, and wherein porous polymer membrane has a pore size larger than the capping agent but smaller than the average particle size of the population of nanoparticles.

45. The system of claim 1 wherein the indicator is a color-retaining indicator.

46. The system of claim 45, wherein the capping agent 4e-does not diffuse out of the receptacle.

* * * * *

UNITED STATES PATENT AND TRADEMARK OFFICE
CERTIFICATE OF CORRECTION

| | |
|---|---|
| PATENT NO. | : 11,853,013 B2 |
| APPLICATION NO. | : 16/901113 |
| DATED | : December 26, 2023 |
| INVENTOR(S) | : Gu et al. |

It is certified that error appears in the above-identified patent and that said Letters Patent is hereby corrected as shown below:

In the Claims

Claim 34, Column 56, Line 11:
Change:
"minutes to 30 days, such as from 1 hour to 30 days."
To read:
--minutes to 30 days.--

Claim 46, Column 56, Line 42:
Change:
"4e-does not diffuse out of the receptacle."
To read:
--does not diffuse out of the receptacle.--

Signed and Sealed this
Twenty-third Day of April, 2024

*Katherine Kelly Vidal*

Katherine Kelly Vidal
*Director of the United States Patent and Trademark Office*